United States Patent
Rohwer et al.

(10) Patent No.: US 9,533,296 B2
(45) Date of Patent: Jan. 3, 2017

(54) BLEACH CATALYSTS

(71) Applicants: BASF SE, Ludwigshafen (DE); Henkel AG & Co. KGaA, Duesseldorf (DE)

(72) Inventors: Hauke Rohwer, Lörrach (DE); Barbara Winkler, Lörrach (DE); Frédérique Wendeborn, Ranspach-le-Haut (FR); Katharina Misteli, Basel (CH)

(73) Assignees: BASF SE, Ludwigshafen (DE); Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/005,288

(22) Filed: Jan. 25, 2016

(65) Prior Publication Data

US 2016/0136627 A1 May 19, 2016

Related U.S. Application Data

(62) Division of application No. 14/697,206, filed on Apr. 27, 2015, which is a division of application No. 13/992,888, filed as application No. PCT/EP2011/072238 on Dec. 8, 2011, now Pat. No. 9,051,285.

(60) Provisional application No. 61/422,251, filed on Dec. 13, 2010.

(30) Foreign Application Priority Data

Dec. 13, 2010 (EP) .................................... 10194758

(51) Int. Cl.
| | | |
|---|---|---|
| C11D 3/28 | (2006.01) |
| C11D 3/33 | (2006.01) |
| B01J 31/02 | (2006.01) |
| C11D 3/39 | (2006.01) |
| C11D 3/30 | (2006.01) |
| B01J 31/18 | (2006.01) |
| C07D 295/15 | (2006.01) |
| C11D 3/32 | (2006.01) |
| C11D 7/32 | (2006.01) |
| C11D 7/34 | (2006.01) |
| C11D 11/02 | (2006.01) |
| D06L 3/02 | (2006.01) |
| B08B 3/08 | (2006.01) |
| C07B 33/00 | (2006.01) |
| C11D 3/34 | (2006.01) |

(52) U.S. Cl.
CPC ......... B01J 31/0271 (2013.01); B01J 31/0202 (2013.01); B01J 31/0204 (2013.01); B01J 31/0218 (2013.01); B01J 31/0245 (2013.01); B01J 31/0247 (2013.01); B01J 31/18 (2013.01); B08B 3/08 (2013.01); C07B 33/00 (2013.01); C07D 295/15 (2013.01); C11D 3/28 (2013.01); C11D 3/30 (2013.01); C11D 3/32 (2013.01); C11D 3/349 (2013.01); C11D 3/391 (2013.01); C11D 3/3902 (2013.01); C11D 3/392 (2013.01); C11D 3/3917 (2013.01); C11D 3/3927 (2013.01); C11D 3/3942 (2013.01); C11D 3/3945 (2013.01); C11D 3/3947 (2013.01); C11D 7/3263 (2013.01); C11D 7/3281 (2013.01); C11D 7/34 (2013.01); C11D 11/02 (2013.01); D06L 3/02 (2013.01); D06L 3/021 (2013.01); *B01J 2231/70* (2013.01); *C11D 3/3481* (2013.01)

(58) Field of Classification Search
CPC ..... C11D 3/391; C11D 3/3927; C11D 3/3942; C11D 3/3945; C11D 3/39497; B08B 3/04; C01B 15/03; C01B 15/037
USPC ............... 510/221, 224, 238, 310, 313, 314, 376,510/501; 8/111, 137; 252/186.26, 186.29, 252/186.41
See application file for complete search history.

(56) References Cited

U.S. PATENT DOCUMENTS

| | | |
|---|---|---|
| 2,670,348 A | 2/1954 | Gregory et al. |
| 2011/0071066 A1 | 3/2011 | Wagner et al. |
| 2013/0117941 A1 | 5/2013 | Frey et al. |

FOREIGN PATENT DOCUMENTS

| | | |
|---|---|---|
| DE | 19639603 A1 | 4/1998 |
| WO | WO-95/07972 A1 | 3/1995 |
| WO | WO-02/060858 A1 | 8/2002 |
| WO | WO-2009/124855 A1 | 10/2009 |

OTHER PUBLICATIONS

XP-002631895, Nov. 30, 2010.*
Jigajinni, V.B., et al., "Hydrazones of Piperidino-N-Acetohydrazide and Morpholino-N-Acetohydrazide of Pharmacological Interest," *Revue Roumaine de Chimie* 21, No. 8 (1976), pp. 1221-1225.
Schlager, L. H., "Derivate von vicinalem Trimethoxybenzol. 2. Mitt.: Amide und Hydrazide der Trimethylgallussäure." *Archiv der Pharmazie* 296, No. 4 (1963), pp. 217-226.
English-language abstract of DE19639603, Apr. 2, 1998.

* cited by examiner

*Primary Examiner* — Gregory R Delcotto
(74) *Attorney, Agent, or Firm* — Marshall, Gerstein & Borun LLP

(57) ABSTRACT

The present invention relates to specific acylhydrazone compounds, their use as oxidation catalysts and to a process for removing stains and soil on textiles and hard surfaces. The compounds are substituted with a specific cyclic ammonium group adjacent to the acyl group. Further aspects of the invention are compositions or formulations comprising such compounds.

15 Claims, No Drawings

BLEACH CATALYSTS

CROSS-REFERENCE TO RELATED APPLICATIONS

This application is a divisional of U.S. patent application Ser. No. 14/697,206, filed Apr. 27, 2015, now U.S. Pat. No. 9,296,713, which is a divisional of 13/992,888, now abandoned filed Jun. 10, 2013, which is a U.S. National Stage of International Application No. PCT/EP2011/072238, filed Dec. 8, 2011, which claims priority to U.S. Provisional Patent Application Number 61/422,251 filed Dec. 13, 2010, wherein the contents of all applications are herein incorporated by reference.

FIELD OF THE INVENTION

The present invention relates to specific acylhydrazone compounds, their use as oxidation catalysts and to a process for removing stains and soil on textiles and hard surfaces. The compounds are substituted with a specific cyclic ammonium group adjacent to the acyl group. Further aspects of the invention are compositions or formulations comprising such compounds.

BACKGROUND OF THE INVENTION

Metal complex catalysts with hydrazide ligands have in generally been described as oxidation catalysts, for example, in DE 196 39 603. However, the compounds disclosed are not active enough.

In WO 2009/124855 metal complex compounds having hydrazide ligands, preferably with electron withdrawing groups adjacent to the acyl group are described. The respective acylhydrazone ligands and their use are also described. The instant compounds differ from those described in WO 2009/124855 by being substituted with a specific cyclic ammonium group adjacent to the acyl group. This specific substitution pattern ensures a significantly higher bleaching activity as compared to prior art complexes or ligands.

The instant compounds are used especially for enhancing the action of $H_2O_2$ or peroxides, for example, in the treatment of textile materials, without at the same time causing any appreciable damage to fibres and dyeings. There is also no appreciable damage to fibres and dyeings if these compounds are used in combination with an enzyme or a mixture of enzymes.

SUMMARY OF THE INVENTION

The instant compounds may also be used as catalysts for oxidation using molecular oxygen and/or air, that is, without peroxide compounds and/or peroxide-forming substances. The bleaching of the fabric can happen during and/or after the treatment of the fibre with the formulation, which comprises the compounds.

The compounds do not cause any odor during use and are significantly more efficient as bleach catalysts as compared to the corresponding open chain tertiary amines.

Metal ions, such as aluminium, zink, manganese, titanium, iron, cobalt, nickel or copper, for example Al(III), Zn(II), Mn(II)-(III)-(IV)-(V), Cu(I)-(II)-(III), Fe(I)-(II)-(III)-(IV), Co(I)-(II)-(III), Ni(I)-(II)-(III), Ti(II)-(III)-(IV) or for instance Mn(II)-(III)-(IV)-(V), Cu(I)-(II)-(III), Fe(I)-(II)-(III)-(IV) and Co(I)-(II)-(III) may be present during the treating process of textile materials but are not necessary for the improved bleaching effect.

Peroxide-containing bleaching agents have long been used in washing and cleaning processes. They have an excellent action at a liquor temperature of 90° C. and above, but their performance noticeably decreases with lower temperatures. Various transition metal ions added in the form of suitable salts, and coordination compounds containing such cations are known to activate $H_2O_2$. In that manner it is possible for the bleaching effect, which is unsatisfactory at lower temperatures, of $H_2O_2$ or precursors that release $H_2O_2$ and of other peroxo compounds, to be increased.

The aim of the present invention is accordingly to provide improved metal free catalysts for oxidation processes that meet the above requirements and, especially, enhance the action of peroxide compounds in the most varied fields of application without causing any appreciable damage.

DETAILED DESCRIPTION OF THE INVENTION

One aspect of the invention is a compound of formula (1)

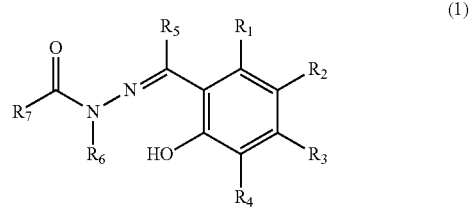

wherein
$R_1$, $R_2$, $R_3$, $R_4$ independently from each other are hydrogen, unsubstituted or substituted $C_1$-$C_{28}$alkyl, $C_1$-$C_{28}$alkoxy, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or napthtyl, wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy;
or $R_1$, $R_2$, $R_3$, $R_4$ independently from each other are $OR_{11}$, $NR_{11}R_{12}$, $NO_2$ or halogen; or
$R_1$ and $R_2$, $R_2$ and $R_3$ or $R_3$ and $R_4$ are linked together to form 1, 2 or 3 carbocyclic or heterocyclic rings, which may be uninterrupted or interrupted by one or more —O—, —S— or —$NR_{13}$— and or which may be further fused with other aromatic rings and/or which may be substituted with one or more $C_1$-$C_6$akyl groups.
$R_5$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy;

$R_6$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphtyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy;

$R_7$ is a group

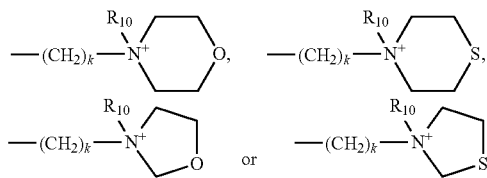

each group with an anion $A^-$;

k is an integer from 1 to 4;

$A^-$ is the anion of an organic or inorganic acid;

$R_{10}$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl;

$R_{11}$, $R_{12}$ independently are hydrogen, $C_1$-$C_{18}$ alkyl or phenyl; or $R_{11}$ and $R_{12}$ together with the nitrogen atom to which they are bonded form a 5 or 6 membered-ring which may contain a further N, O or S atom.

$R_{13}$ denotes hydrogen or $C_1$-$C_{18}$alkyl.

Where applicable the acyl hydrazone derivatives can be in their E- or Z-configuration. When $R_6$ is hydrogen the compound of formula (1) may be in one of its tautomeric forms or as a mixture of its different tautomeric forms.

The compounds of formula (1) may also be ligands in metal complexes, such as Mn(II)-(III)-(IV)-(V), Cu(I)-(II)-(III), Fe(I)-(II)-(III)-(IV), Co(I)-(II)-(III). These complexes can also be used in cleaning and bleaching processes, in particular in the context of washing processes. Similar complexes and their use have been described in WO 91/224855 and WO 2009/124855.

The inorganic or organic anion $A^-$ may be an anion such as $RCOO^-$, $ClO_4^-$, $BF_4^-$, $PF_6^-$, $RSO_3^-$, $RSO_4^-$, $SO_4^{2-}$, $H_2PO_4^{2-}$, $HPO_4^{2-}$, $OCN^-$, $SCN^-$, $NO_3^-$, $F^-$, $Cl^-$, $Br^-$ or $HCO_3^-$, with R being hydrogen, optionally substituted $C_1$-$C_{24}$alkyl or optionally substituted aryl. Examples are lactic acid, citric acid, tartaric acid, succinic acid.

For anions with a charge greater than −1 the charge balance is established by additional cations, such as $H^+$, $Na^+$, $K^+$, $NH_4^+$.

For example $A^-$ is $RCOO^-$, $ClO_4^-$, $BF_4^-$, $PF_6^-$, $RSO_3^-$, $RSO_4^-$, $SO_4^{2-}$, $NO_3^-$, $F^-$, $Cl^-$, $Br^-$ and $I^-$ wherein R is linear or branched $C_1$-$C_{18}$alkyl or phenyl.

In general unsubstituted alkyl, heteroalkyl, cycloalkyl, alkenyl, cycloalkenyl, alkinyl, phenyl, naphthyl, aralkyl, heteroaralkyl and cycloheteroalkyl are preferred.

Cyclic substituents are preferably 5-, 6- or 7-membered rings, 6-membered rings are preferred.

Aryl is phenyl or naphthyl in all cases where applicable.

The $C_1$-$C_{18}$alkyl radicals mentioned for the compounds of formula (1) are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

In the compounds of formulae (1) halogen is preferably chlorine, bromine or fluorine, with special preference being given to chlorine.

Examples of aryl radicals that come into consideration for the compounds of formula (1) are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1$-$C_4$alkyl, $C_1$-$C_4$alkoxy, phenyl and hydroxy.

Special preference is given to the corresponding phenyl radicals.

$C_3$-$C_{12}$cycloalkyl refers to saturated cyclic hydrocarbons. $C_3$-$C_{12}$cycloalkyl is for example cyclopropyl, cyclobutyl, cyclopentyl, cyclohexyl, trimethylcyclohexyl, menthyl, thujyl, bornyl, 1-adamantyl oder 2-adamantyl.

$C_2$-$C_{18}$alkenyl is for example vinyl, allyl, 2-propen-2-yl, 2-buten-1-yl, 3-buten-1-yl, 1,3-butadien-2-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, or signifies different isomers of hexenyl, octenyl, nonenyl, decenyl or dodecenyl.

$C_3$-$C_{12}$ cycloalkenyl refers to unsaturated hydrocarbon residues containing one or multiple double bonds such, 2-cyclobuten-1-yl, 2-cyclopenten-1-yl, 2-cyclohexen-1-yl, 3-cyclohexen-1-yl 1,2,4-cyclohexadien-1-yl, 1-p-menthen-8-yl, 4(10)-thujen-10-yl, 2-norbornen-1-yl, 2,5-norbornadien-1-yl or 7,7-dimethyl-2,4-norcaradien-3-yl.

$C_7$-$C_9$ aralkyl is for example benzyl, β-phenyl-ethyl, α,α-dimethylbenzyl. $C_5$-$C_{16}$heteroaralkyl signifies for example a $C_1$-$C_8$ alkyl moiety which is substituted with a $C_4$-$C_8$heteroaryl group, preferably with a $C_5$-$C_6$heteroraryl group.

$C_5$-$C_6$heteroaryl is for example pyridine or pyrimidine.

In a specific embodiment the compound is of formula (1)

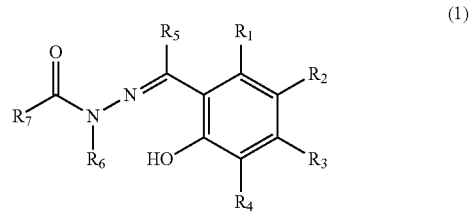

wherein $R_1$, $R_2$, $R_3$, $R_4$ independently from each other are hydrogen, $C_1$-$C_8$alkyl, $C_1$-$C_8$alkoxy, halogen, $OR_{11}$ or $NR_{11}R_{12}$;

$R_5$ denotes hydrogen or $C_1$-$C_{18}$alkyl;

$R_6$ denotes hydrogen or $C_1$-$C_{18}$alkyl;

$R_7$ is a group

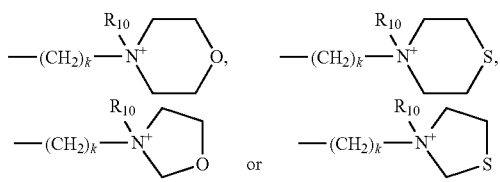

each group with an anion $A^-$;
k is an integer from 1 to 4;
$A^-$ is $Cl^-$, $Br^-$, $ClO_4^-$, $NO_3^-$, $HSO_4^-$, $BF_4^-$ or $PF_6^-$;
$R_{10}$ denotes hydrogen or $C_1$-$C_{18}$alkyl;
$R_{11}$, $R_{12}$ independently are hydrogen, $C_1$-$C_{18}$alkyl or phenyl;
$R_{13}$ denotes hydrogen or $C_1$-$C_4$alkyl.

For example in the compounds of formula (1) $R_1$, $R_2$, $R_3$, $R_4$ independently from each other are hydrogen, OH, methoxy, halogen or methyl;
$R_5$ denotes hydrogen or methyl;
$R_6$ denotes hydrogen or methyl;
$R_7$ is a group

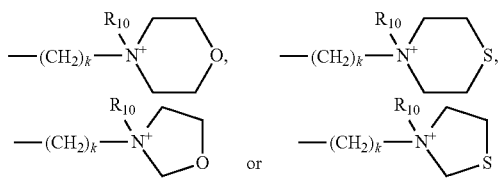

each group with an anion $A^-$;
k is an integer from 1 to 2;
$A^-$ is $Cl^-$, Br, $ClO_4^-$, $NO_3^-$, $HSO_4^-$, $BF_4^-$ or $PF_6^-$;
$R_{10}$ denotes hydrogen or $C_1$-$C_4$alkyl.

For instance in the compounds of formula (1) $R_1$, $R_2$, $R_3$, $R_4$ independently from each other are hydrogen, OH, or methyl;
$R_5$ denotes hydrogen;
$R_6$ denotes hydrogen;
$R_7$ is a group

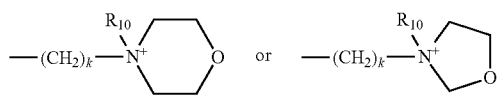

each group with an anion $A^-$;
k is 1;
$A^-$ is $Cl^-$, $Br^-$, $ClO_4^-$, $NO_3^-$, $HSO_4^-$, $BF_4^-$ or $PF_6^-$;
$R_{10}$ denotes methyl.

Preferred is a compound of formula (1) wherein
$R_1$, $R_2$, $R_3$, $R_4$ are hydrogen;
$R_5$ denotes hydrogen;
$R_6$ denotes hydrogen;
$R_7$ is a group

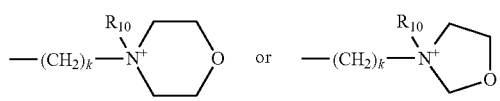

each group with an anion $A^-$;
k is 1;
$A^-$ is $Cl^-$ or $Br^-$,
$R_{10}$ denotes methyl.

The compounds can be prepared according to standard procedures by reacting a carbonyl compound, such as an aldehyde with a primary amine to form the corresponding Schiff base, in particular with a hydrazide and with a carbonyl compound wherein the substituents are as defined above. The compounds may be, for example, prepared in analogy to those described in WO 2009/124855.

The compounds of formula (1) including the above described preferences are novel compounds with the exception of (N-[(2-hydroxyphenyl)methyleneamino]-2-(4-methylmorpholin-4-ium-4-yl)acetamide chloride, which is excluded from the scope of compounds according to formula (1). The use of this specific compound, however, is also novel.

The compounds of formula (1) are useful as catalysts for oxidation reactions, for the bleaching of stains and soil on textiles or for the cleaning of hard surfaces.

Therefore, another aspect of the invention is a composition comprising
a) $H_2O_2$ or a precursor of $H_2O_2$; and
b) a compound of formula (1) as described above.

The amount of component b), compound of formula (1), in the composition may vary from 0.00001 weight-% to 1 weight-%, preferably from 0.0001 weight-% to 0.1 weight-%, based on the weight of the total composition.

In many cases in the composition as described above additional bleach activator is present. Suitable bleach activators are outlined below.

The amount of bleach activator in the composition may vary from 0.1 weight-% to 12 weight-%, preferably from 0.5 weight-% to 10 weight-%, based on the weight of the total composition.

It may be of advantage when the composition as described above optionally contains one or more metal chelating agents (sequestrants), such as hydroxyethyldiphosphonate (HEDP). More generally, chelating agents suitable for use herein can be selected from the group consisting of amino carboxylates, amino phosphonates, polyfunctionally-substituted aromatic chelating agents and mixtures thereof. Other suitable chelating agents for use herein are the commercial DEQUEST series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof and mixtures thereof.

Aminophosphonates are also suitable for use as chelating agents in the compositions of the invention when at least low levels of total phosphorus are permitted in detergent compositions, and include ethylenediaminetetrakis (methylenephosphonates).

Further biodegradable sequestrants are, for example, aminoacid acetates, such as Trilon M (BASF) and Dissolvine GL (AKZO), as well as asparaginic acid derivatives, such as Baypure CX.

Preferably, the aminophosphonates do not contain alkyl or alkenyl groups with more than about 6 carbon atoms.

A highly preferred biodegradable chelator for use herein is ethylenediamine disuccinate ("EDDS").

Preferred are the following chelating agents (sequestrants): Citric acid, Oxalic acid, methyl-glycine-diacetic acid (MGDA), ethylenediamine-N,N'-disuccinic acid (EDDS), 1-hydroxy ethylidene-1,1-diphosphonic acid (HEDP).

If utilized, these chelating agents or transition-metal selective sequestrants will generally be present from about 0.001 weight-% to about 10 weight-%, more preferably from about 0.05 weight-% to about 1 weight-%, based on the weight of the total composition.

Component a) of the composition may be $H_2O_2$, a precursor of $H_2O_2$ or a peroxide forming substance. Preferred are precursors of $H_2O_2$, such as peroxides or peracids outlined below.

As precursors of $H_2O_2$ peroxides come into consideration. I. e. every compound which is capable of yielding hydrogen peroxide in aqueous solutions, for example, the organic and inorganic peroxides known in the literature and available commercially that bleach textile materials at conventional washing temperatures, for example at from 10 to 95° C.

Preferably, however, inorganic peroxides are used, for example persulfates, perborates, percarbonates and/or persilicates. They are typically used in an amount of 2-80 wt-%, preferably of 4-30 wt-%, based on the weight of the composition.

Typically the compound of formula (1) is present in the composition in an amount of 0.05-15 wt-%, preferably from 0.1 to 10 wt-%, based on the weight of the total composition.

Examples of suitable inorganic peroxides are sodium perborate tetrahydrate or sodium perborate monohydrate, sodium percarbonate, inorganic peroxyacid compounds, such as for example potassium monopersulphate (MPS). If organic or inorganic peroxyacids are used as the peroxygen compound, the amount thereof will normally be within the range of about 2-80 wt-%, preferably from 4-30 wt-%, based on the weight of the composition.

The organic peroxides are, for example, mono- or polyperoxides, urea peroxides, a combination of a $C_1$-$C_4$alkanol oxidase and $C_1$-$C_4$alkanol (Such as methanol oxidase and ethanol as described in WO95/07972), alkylhydroxy peroxides, such as cumene hydroperoxide and t-butyl hydroperoxide.

The peroxides may be in a variety of crystalline forms and have different water contents, and they may also be used together with other inorganic or organic compounds in order to improve their storage stability.

As oxidants, peroxo acids can also be used. One example are organic mono peracids of formula 9

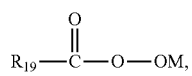

wherein
M signifies hydrogen or a cation,
$R_{19}$ signifies unsubstituted $C_1$-$C_{18}$alkyl; substituted $C_1$-$C_{18}$alkyl; unsubstituted aryl; substituted aryl; —($C_1$-$C_6$alkylene)-aryl, wherein the alkylene and/or the alkyl group may be substituted; and phthalimido$C_1$-$C_8$alkylene, wherein the phthalimido and/or the alkylene group may be substituted.

Preferred mono organic peroxy acids and their salts are those of formula

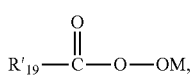

wherein
M signifies hydrogen or an alkali metal, and
$R'_{19}$ signifies unsubstituted $C_1$-$C_4$alkyl; phenyl; —$C_1$-$C_2$alkylene-phenyl or phthalimido$C_1$-$C_8$alkylene.

Especially preferred is $CH_3COOOH$ and its alkali salts.

Especially preferred is also s-phthalimido peroxy hexanoic acid and its alkali salts.

Also suitable are diperoxyacids, for example, 1,12-diperoxydodecanedioic acid (DPDA), 1,9-diperoxyazelaic acid, diperoxybrassilic acid, diperoxysebasic acid, diperoxyisophthalic acid, 2-decyldiperoxybutane-1,4-diotic acid and 4,4'-sulphonylbisperoxybenzoic acid.

In some cases the use of an additional bleach activator may be of advantage.

The term bleach activator is frequently used as a synonym for peroxyacid bleach precursor. All the above mentioned peroxy compounds may be utilized alone or in conjunction with a peroxyacid bleach precursor.

Such precursors are the corresponding carboxyacid or the corresponding carboxyanhydride or the corresponding carbonylchlorid, or amides, or esters, which can form the peroxy acids on perhydrolysis. Such reactions are commonly known.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412,934 and 4,675,393.

Suitable bleach activators include the bleach activators, that carry O- and/or N-acyl groups and/or unsubstituted or substituted benzoyl groups. Preference is given to polyacylated alkylenediamines, especially tetraacetylethylenediamine (TAED); acylated glycolurils, especially tetraacetyl glycol urea (TAGU), N,N-diacetyl-N,N-dimethylurea (DDU); sodium-4-benzoyloxy benzene sulphonate (SBOBS); sodium-1-methyl-2-benzoyloxy benzene-4-sulphonate; sodium-4-methyl-3-benzoloxy benzoate; trimethyl ammonium toluyloxy-benzene sulphonate; acylated triazine derivatives, especially 1,5-diacetyl-2,4-dioxohexahydro-1,3,5-triazine (DADHT); compounds of formula (6):

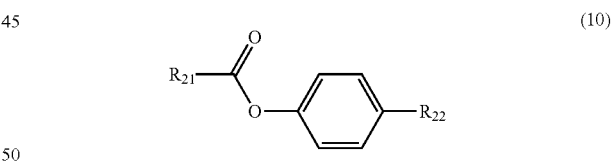

wherein $R_{22}$ is a sulfonate group, a carboxylic acid group or a carboxylate group, and wherein $R_{21}$ is linear or branched ($C_7$-$C_{15}$)alkyl, especially activators known under the names SNOBS, SLOBS and DOBA; acylated polyhydric alcohols, especially triacetin, ethylene glycol diacetate and 2,5-diacetoxy-2,5-dihydrofuran; and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A-44 43 177. Nitrile compounds that form perimine acids with peroxides also come into consideration as bleach activators.

Another useful class of peroxyacid bleach precursors is that of the cationic i.e. quaternary ammonium substituted peroxyacid precursors as disclosed in U.S. Pat. Nos. 4,751,015 and 4,397,757, in EP-A0284292 and EP-A-331,229. Examples of peroxyacid bleach precursors of this class are: 2-(N,N,N-trimethyl ammonium)ethyl sodium-4-sulphonphenyl carbonate chloride—(SPCC), N-octyl,N,N-dimehyl-N10-carbophenoxy decyl ammonium chloride—(ODC), 3-(N,N,N-trimethyl ammonium) propyl sodium-4-sulphophenyl carboxylate and N,N,N-trimethyl ammonium toluyloxy benzene sulphonate.

A further special class of bleach precursors is formed by the cationic nitriles as disclosed in EP-A-303,520, WO 96/40661 and in European Patent Specification No.'s 458,396, 790244 and 464,880. These cationic nitriles also known as nitril quats have the formula

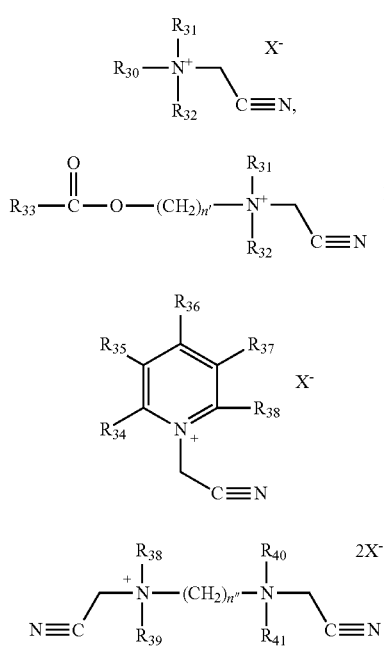

wherein $R_{30}$ is a $C_1$-$C_{24}$alkyl; a $C_1$-$C_{24}$alkenyl; an alkaryl having a $C_1$-$C_{24}$alkyl; a substituted $C_1$-$C_{24}$alkyl; a substituted $C_1$-$C_{24}$alkenyl; a substituted aryl, $R_{31}$ and $R_{32}$ are each independently a $C_1$-$C_3$alkyl; hydroxyalkyl having 1 to 3 carbon atoms, —$(C_2H_4O)_n$H, n being 1 to 6; —$CH_2$—CN $R_{33}$ is a $C_1$-$C_{20}$alkyl; a $C_1$-$C_{20}$alkenyl; a substituted $C_1$-$C_{20}$alkyl; a substituted $C_1$-$C_{20}$alkenyl; an alkaryl having a $C_1$-$C_{24}$alkyl and at least one other substituent, $R_{34}$, $R_{35}$, $R_{36}$, $R_{37}$ and $R_{38}$ are each independently hydrogen, a $C_1$-$C_{10}$alkyl, a $C_1$-$C_{10}$alkenyl, a substituted $C_1$-$C_{10}$alkyl, a substituted $C_1$-$C_{10}$alkenyl, carboxyl, sulfonyl or cyano $R_{38}$, $R_{39}$, $R_{40}$ and $R_{41}$ are each independently a $C_1$-$C_6$alkyl, n' is an integer from 1 to 3, n" is an integer from 1 to 16, and X is an anion.

Other nitril quats have the following formula

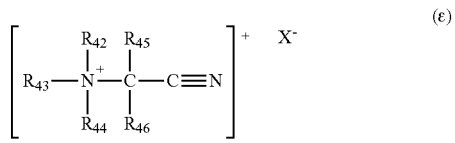

wherein $R_{42}$ and $R_{43}$ form, together with the nitrogen atom to which they are bonded, a ring comprising 4 to 6 carbon atoms, this ring may also be substituted by $C_1$-$C_5$-alkyl, $C_1$-$C_5$-alkoxy, $C_1$-$C_5$-alkanoyl, phenyl, amino, ammonium, cyano, cyanamino or chloro and 1 or 2 carbon atom(s) of this ring may also be substituted by a nitrogen atom, by a oxygen atom, by a N—$R_{47}$-group and/or by a $R_{44}$—N—$R_{47}$-group, wherein $R_{47}$ is hydrogen, $C_1$-$C_5$-alkyl, $C_2$-$C_5$-alkenyl, $C_2$-$C_5$-alkinyl, phenyl, $C_7$-$C_9$-aralkyl, $C_5$-$C_7$-cycloalkyl, $C_1$-$C_5$-alkanoyl, cyanomethyl or cyano, $R_{44}$ is $C_1$-$C_{24}$-, preferably $C_1$-$C_4$-alkyl; $C_2$-$C_{24}$-alkenyl, preferably $C_2$-$C_4$-alkenyl, cyanomethyl or $C_1$-$C_4$-alkoxy-$C_1$-$C_4$-alkyl, $R_{45}$ and $R_{46}$ are independently from each other hydrogen; $C_1$-$C_4$-alkyl; $C_1$-$C_4$-alkenyl; $C_1$-$C_4$-alkoxy-$C_1$-$C_4$-alkyl; phenyl or $C_1$-$C_3$-alkylphenyl, preferably hydrogen, methyl or phenyl, whereby preferably the moiety $R_{45}$ signifies hydrogen, if $R_{46}$ is not hydrogen, and $X^-$ is an anion.

Suitable examples of nitril quats of formula (s) are

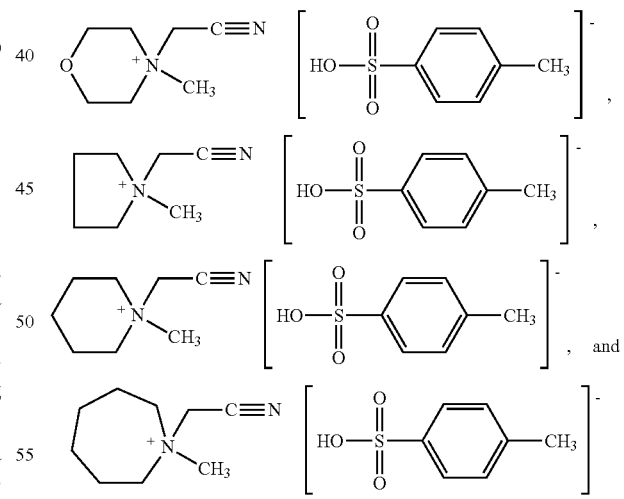

Other nitrile quats have the formula

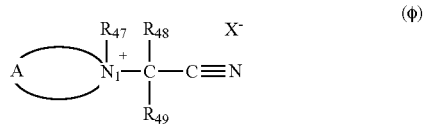

-continued

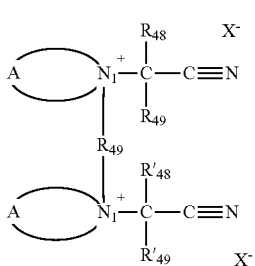

wherein
A is a saturated ring formed by a plurality of atoms in addition to the $N_1$ atom, the saturated ring atoms to include at least one carbon atom and at least one heteroatom in addition to the $N_1$ atom, the said one heteroatom selected from the group consisting of O, S and N atoms, the substituent $R_{47}$ bound to the $N_1$ atom of the Formula (φ) structure is (a) a $C_1$-$C_8$-alkyl or alkoxylated alkyl where the alkoxy is $C_2$-4, (b) a $C_4$-$C_{24}$cycloalkyl, (c) a $C_7$-$C_{24}$alkaryl, (d) a repeating or nonrepeating alkoxy or alkoxylated alcohol, where the alkoxy unit is $C_2$-4, or (e) —$CR_{50}R_{51}$—C≡N where $R_{50}$ and $R_{51}$ are each H, a $C_1$-$C_{24}$alkyl, cycloalkyl, or alkaryl, or a repeating or nonrepeating alkoxyl or alkoxylated alcohol where the alkoxy unit is $C_2$-$C_4$, in Formula (φ) at least one of the $R_{48}$ and $R_{49}$ substituents is H and the other of $R_{48}$ and $R_{49}$ is H, a $C_1$-$C_{24}$alkyl, cycloalkyl, or alkaryl, or a repeating or nonrepeating alkoxyl or alkoxylated alcohol where the alkoxy unit is $C_2$-4, and Y is at least one counterion.

In a preferred embodiment of the invention the compounds of formula (1) are used together with a peroxide or peroxide precursor and a bleach activator which is selected from the group consisting of tetraacetylethylenediamine, pentaacetylglucose, sodium octanoyloxybenzenesulfonate, sodium nonanoyloxybenzenesulfonate, sodium decanoyloxybenzenesulfonate, sodium undecanoyloxybenzenesulfonate, sodium dodecanoyloxybenzenesulfonate, octanoyloxybenzoic acid, nonanoyloxybenzoic acid, decanoyloxybenzoic acid, undecanoyloxybenzoic acid, dodecanoyloxybenzoic acid, octanoyloxybenzene, nonanoyloxybenzene, decanoyloxybenzene, undecanoyloxybenzene and dodecanoyloxybenzene.

The activators may be used in an amount of up to 12 wt-%, preferably from 0.5-10 wt-% based on the total weight of the composition.

Since the compounds of the invention are used for the bleaching of stains or of soiling on textile materials or dishes in the context of a washing process or by the direct application of a stain remover, a further aspect of the invention is a detergent, cleaning or bleaching composition comprising
I) from 0 to 50 wt-%, based on the total weight of the composition, A) of at least one anionic surfactant and/or B) of a non-ionic surfactant,
II) from 0 to 70 wt-%, based on the total weight of the composition, C) of at least one builder substance,
Ill) from 1-99 wt-%, based on the total weight of the composition, D) of at least one peroxide and/or one peroxide-activator, $O_2$ and/or air,
IV) E) at least one compound of formula (1) according to claim 1 to 5 in an amount that, in the liquor, gives a concentration of from 0.5 to 100 mg/litre of liquor, when from 0.5 to 50 g/litre of the detergent, cleaning, disinfecting or bleaching agent are added to the liquor,
V) from 0-20 wt-%, based on the total weight of the composition, of at least one further additive, and
VI) water ad 100 wt-%, based on the total weight of the composition.

The composition may optionally also contain water, or a filler material, such as $Na_2SO_4$. The sum of the components I) to IV) and optionally further components adds to 100%.

All wt-% are based on the total weight of the detergent, cleaning or bleaching composition.

The detergent, cleaning or bleaching compositions can be any kind of industrial or domestic cleaning or bleaching formulation.

The detergents may be in solid, liquid, gel-like or paste-like form. The detergents may also be in the form of powders or (super-)compact powders or granules, in the form of single- or multi-layer tablets (tabs), in the form of washing agent bars, washing agent blocks, washing agent sheets, washing agent pastes or washing agent gels, or in the form of powders, pastes, gels or liquids used in capsules or in pouches (sachets).

When the composition is used in a washing process the concentration of the $H_2O_2$ or its precursor, such as perborate or percarbonate may vary in the range from 0.01 g/L to g/L, preferably 0.03 g/L to 8 g/L and more preferably from 0.05 g/L to 2.5 g/L. If an additional activator is used, the activator, such as tetraacetylethylenediamine may vary from 0.01 g/L to 5 g/L, preferably from 0.015 g/L to 3 g/L, more preferably from 0.015 g/L to 1 g/L. The compound of formula (1) may vary from 1 μmol/L to 1 mmol/L, preferably from 3 μmol/L to 0.5 mmol/L, more preferably from 5 μmol/L to 0.3 mmol/L.

It is also possible to use additional bleach catalysts, which are commonly known, for example transition metal complexes as disclosed in EP 1194514, EP 1383857 or WO04/007657.

When the detergent compositions according to the invention comprise a component A) and/or B), the amount thereof is preferably from 0.5 to 50 wt-%, especially from 0.5 to 30 wt-%.

When the detergent compositions according to the invention comprise a component C), the amount thereof is preferably from 1 to 70 wt-%, especially from 1 to 50 wt-%. Special preference is given to an amount of from 5 to 50 wt-% and especially an amount of from 10 to 50 wt-%.

The detergent composition according to the invention can be, for example, a peroxide-containing heavy-duty detergent or a separate bleaching additive, or a stain remover that is to be applied directly. A bleaching additive is used for removing coloured stains on textiles in a separate liquor before the clothes are washed with a detergent. A bleaching additive can also be used in a liquor together with a detergent.

Stain removers can be applied directly to the textile in question and are used especially for pretreatment in the event of heavy local soiling.

The stain remover can be applied in liquid form, by a spraying method or in the form of a solid substance, such as a powder especially as a granule.

The anionic surfactant A) can be, for example, a sulfate, sulfonate or carboxylate surfactant or a mixture thereof. Preference is given to alkylbenzenesulfonates, alkyl sulfates, alkyl ether sulfates, olefin sulfonates, fatty acid salts, alkyl and alkenyl ether carboxylates or to an a-sulfonic fatty acid salt or an ester thereof.

Preferred sulfonates are, for example, alkylbenzenesulfonates having from 10 to 20 carbon atoms in the alkyl radical, alkyl sulfates having from 8 to 18 carbon atoms in the alkyl radical, alkyl ether sulfates having from 8 to 18 carbon atoms in the alkyl radical, and fatty acid salts derived from palm oil or tallow and having from 8 to 18 carbon atoms in the alkyl moiety. The average molar number of ethylene oxide units added to the alkyl ether sulfates is from 1 to 20, preferably from 1 to 10. The cation in the anionic surfactants is preferably an alkaline metal cation, especially sodium or potassium, more especially sodium. Preferred carboxylates are alkali metal sarcosinates of formula $R_{19}$—$CON(R_{20})CH_2COOM_1$ wherein $R_{19}$ is $C_9$-$C_{17}$alkyl or $C_9$-$C_{17}$alkenyl, $R_{20}$ is $C_1$-$C_4$alkyl and $M_1$ is an alkali metal, especially sodium.

The non-ionic surfactant B) may be, for example, a primary or secondary alcohol ethoxylate, especially a $C_8$-$C_{20}$ aliphatic alcohol ethoxylated with an average of from 1 to 20 mol of ethylene oxide per alcohol group. Preference is given to primary and secondary $C_{10}$-$C_{15}$ aliphatic alcohols ethoxylated with an average of from 1 to 10 mol of ethylene oxide per alcohol group. Non-ethoxylated non-ionic surfactants, for example alkylpolyglycosides, glycerol monoethers and polyhydroxyamides (glucamide), may likewise be used.

The total amount of anionic and non-ionic surfactants is preferably from 3 to 50 wt-%, especially from 5 to 40 wt-% and more especially from 5 to 30 wt-%. The lower limit of those surfactants to which even greater preference is given is 5 wt-%.

As builder substance C) there come into consideration, for example, alkali metal phosphates, especially tripolyphosphates, carbonates and hydrogen carbonates, especially their sodium salts, silicates, aluminum silicates, polycarboxylates, polycarboxylic acids, organic phosphonates, aminoalkylenepoly(alkylenephosphonates) and mixtures of such compounds.

Silicates that are especially suitable are sodium salts of crystalline layered silicates of the formula $NaHSitO_{2t+1} \cdot pH_2O$ or $Na_2Si_2O_{2t+1} \cdot pH_2O$ wherein t is a number from 1.9 to 4 and p is a number from 0 to 20.

Among the aluminum silicates, preference is given to those commercially available under the names zeolite A, B, X and HS, and also to mixtures comprising two or more of such components. Special preference is given to zeolite A.

Among the polycarboxylates, preference is given to polyhydroxycarboxylates, especially citrates, and acrylates, and also to copolymers thereof with maleic anhydride. Preferred polycarboxylic acids are nitrilotriacetic acid, ethylenediaminetetraacetic acid and ethylenediamine disuccinate either in racemic form or in the enantiomerically pure (S,S) form.

Biodegradable options are, for example, aminoacid acetates, such as Trilon M (BASF) and Dissolvine GL (AKZO), as well as asparaginic acid derivatives, such as Baypure CX (Lanxess).

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid and diethylenetriaminepentamethylenephosphonic acid, and also salts thereof. Also preferred polyphosphonates have the following formula

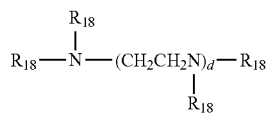

wherein
$R_{18}$ is $CH_2PO_3H_2$ or a water soluble salt thereof and
d is an integer of the value 0, 1, 2 or 3.

Especially preferred are the polyphosphonates wherein d is an integer of the value of 1.

The compositions may comprise, in addition to the combination according to the invention, one or more optical brighteners, for example from the classes bis-triazinylamino-stilbenedisulfonic acid, bis-triazolyl-stilbenedisulfonic acid, bis-styryl-biphenyl or bis-benzofuranylbiphenyl, a bis-benzoxalyl derivative, bis-benzimidazolyl derivative or coumarin derivative or a pyrazoline derivative.

The compositions may furthermore comprise one or more further additives. Such additives are, for example, dirt-suspending agents, for example sodium carboxymethylcellulose; pH regulators, for example alkali metal or alkaline earth metal silicates; foam regulators, for example soap; salts for adjusting the spray drying and the granulating properties, for example sodium sulfate; perfumes; and also, if appropriate, antistatics and softening agents such as, for example, smectite; bleaching agents; pigments; and/or toning agents. These constituents should especially be stable to any bleaching agent employed.

If the detergent composition is used in an automatic dishwasher it is also common to use silver-corrosion inhibitors.

Such auxiliaries are added in a total amount of from 0.1-20 wt-%, preferably from 0.5-10 wt-%, especially from 0.5-5 wt-%, based on the total weight of the detergent formulation.

Furthermore, the detergent may optionally also comprise enzymes. Enzymes can be added for the purpose of stain removal. The enzymes usually improve the action on stains caused by protein or starch, such as, for example, blood, milk, grass or fruit juices. Preferred enzymes are cellulases and proteases, especially proteases. Cellulases are enzymes that react with cellulose and its derivatives and hydrolyse them to form glucose, cellobiose and cellooligosaccharides. Cellulases remove dirt and, in addition, have the effect of enhancing the soft handle of the fabric.

Examples of customary enzymes include, but are by no means limited to, the following:
proteases as described in U.S. Pat. No. 6,242,405, column 14, lines 21 to 32;
lipases as described in U.S. Pat. No. 6,242,405, column 14, lines 33 to 46;
amylases as described in U.S. Pat. No. 6,242,405, column 14, lines 47 to 56; and
cellulases as described in U.S. Pat. No. 6,242,405, column 14, lines 57 to 64.

Commercially available detergent proteases, such as Alcalase®, Esperase®, Everlase®, Savinase®, Kannase® and Durazym®, are sold e.g. by NOVOZYMES A/S.

Commercially available detergent amylases, such as Termamyl®, Duramyl®, Stainzyme®, Natalase®, Ban® and Fungamyl®, are sold e.g. by NOVOZYMES A/S.

Commercially available detergent cellulases, such as Celluzyme®, Carezyme® and Endolase®, are sold e.g. by NOVOZYMES A/S.

Commercially available detergent lipases, such as Lipolase®, Lipolase Ultra® and Lipoprime®, are sold e.g. by NOVOZYMES A/S.

Suitable mannanases, such as Mannanaway®, are sold by NOVOZYMES A/S.

Beside in laundry care products, in a dishwashing detergents, especially in a composition used in automatic dishwashers the following enzymes are also commonly used:

proteases, amylases, pullulanases, cutinases and lipases, for example proteases such as BLAP®, Optimase®, Opticlean®, Maxacal®, Maxapem®, Esperase® and/or Savinase®, amylases such as Termamyl®, Amylase-LT®, Maxamyl® and/or Duramyl®, lipases such as Lipolase®, Lipomax®, Lumafast® and/or Lipozym®. The enzymes which may be used can, as described e.g. in International Patent Applications WO 92/11347 and WO 94/23005, be adsorbed on carriers and/or embedded in encapsulating substances in order to safeguard them against premature inactivation. They are present in the cleaning formulations according to the invention preferably in amounts not exceeding 5 wt-%, especially in amounts of from 0.1 wt-% to 1.2 wt-%.

Amylases: The present invention preferably makes use of amylases having improved stability in detergents, especially improved oxidative stability. Such amylases are non-limitingly illustrated by the following: (a) An amylase according to WO 94/02597, Novo Nordisk A/S, published Feb. 3, 1994, as further illustrated by a mutant in which substitution is made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens*, *B. subtilis*, or *B. stearothermophilus*; (b) Stability-enhanced amylases as described by Genencor International in a paper entitled "Oxidatively Resistant alpha-Amylases" presented at the 207th American Chemical Society National Meeting, Mar. 13-17 1994, by C. Mitchinson. Therein it was noted that bleaches in automatic dishwashing detergents inactivate alpha-amylases but that improved oxidative stability amylases have been made by Genencor from *B. licheniformis* NCIB8061. Any other oxidative stability-enhanced amylase can be used.

Proteases: Protease enzymes are usually present in preferred embodiments of the invention at levels between 0.001 wt-% and 5 wt-%. The proteolytic enzyme can be of animal, vegetable or microorganism (preferred) origin. More preferred is serine proteolytic enzyme of bacterial origin. Purified or nonpurified forms of enzyme may be used. Proteolytic enzymes produced by chemically or genetically modified mutants are included by definition, as are close structural enzyme variants. Suitable commercial proteolytic enzymes include Alcalase®, Esperase®, Durazyme®, Savinase®, Maxatase®, Maxacal®, and Maxapem® 15 (protein engineered Maxacal). Purafect® and subtilisin BPN and BPN' are also commercially available.

When present, lipases comprise from about 0.001 wt-% to about 0.01 wt-% of the instant compositions and are optionally combined with from about 1 wt-% to about 5 wt-% of a surfactant having limesoap-dispersing properties, such as an alkyldimethylamine N-oxide or a sulfobetaine. Suitable lipases for use herein include those of bacterial, animal and fungal origin, including those from chemically or genetically modified mutants.

When incorporating lipases into the instant compositions, their stability and effectiveness may in certain instances be enhanced by combining them with small amounts (e.g., less than 0.5 wt-% of the composition) of oily but non-hydrolyzing materials.

The enzymes, when used, may be present in a total amount of from 0.01 to 5 wt-%, especially from 0.05 to 5 wt-% and more especially from 0.1 to 4 wt-%, based on the total weight of the detergent formulation.

If the detergent formulation is a dishwashing detergent formulation, more preferably an automatic dishwashing detergent formulation, then it can optionally also comprise from about 0.001 wt-% to about 10 wt-%, preferably from about 0.005 wt-% to about 8 wt-%, most preferably from about 0.01 wt-% to about 6 wt-% of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

In order to enhance the bleaching action, the compositions may, in addition to comprising the catalysts described herein, also comprise photocatalysts the action of which is based on the generation of singlet oxygen.

Further preferred additives to the compositions according to the invention are dye-fixing agents and/or polymers which, during the washing of textiles, prevent staining caused by dyes in the washing liquor that have been released from the textiles under the washing conditions. Such polymers are preferably polyvinylpyrrolidones, polyvinylimidazoles or polyvinylpyridine-N-oxides, which may have been modified by the incorporation of anionic or cationic substituents, especially those having a molecular weight in the range of from 5000 to 60 000, more especially from 10 000 to 50 000. Such polymers are usually used in a total amount of from 0.01 to 5 wt-%, especially from 0.05 to 5 wt-%, more especially from 0.1 to 2 wt-%, based on the total weight of the detergent formulation. Preferred polymers are those mentioned in WO-A-02/02865 (see especially page 1, last paragraph and page 2, first paragraph) and those in WO-A-04/05688.

When the inventive detergent composition is used as hardsurface cleaner, especially when the composition is used in automatic dishwasher formulations then, it has been found out, that it is preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions.

Other examples for foam suppressors are paraffin, paraffin/alcohol combinations, or bisfatty acid amides.

The dishwashing detergent formulations, more preferably automatic dishwashing detergent formulations herein may also optionally contain one or more heavy metal chelating agents, such as hydroxyethyldiphosphonate (HEDP). More generally, chelating agents suitable for use herein can be selected from the group consisting of amino carboxylates, amino phosphonates, polyfunctionally-substituted aromatic chelating agents and mixtures thereof. Other suitable chelating agents for use herein are the commercial DEQUEST series, and chelants from Nalco, Inc.

Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof and mixtures thereof.

Aminophosphonates are also suitable for use as chelating agents in the compositions of the invention when at least low levels of total phosphorus are permitted in detergent compositions, and include ethylenediaminetetrakis (methylenephosphonates).

Further biodegradable sequestrants are, for example, aminoacid acetates, such as Trilon M (BASF) and Dissolvine GL (AKZO), as well as asparaginic acid derivatives, such as Baypure CX.

Preferably, the aminophosphonates do not contain alkyl or alkenyl groups with more than about 6 carbon atoms.

A highly preferred biodegradable chelator for use herein is ethylenediamine disuccinate ("EDDS").

If utilized, these chelating agents or transition-metal selective sequestrants will generally comprise from about 0.001 wt-% to about 10 wt-%, more preferably from about 0.05 wt-% to about 1 wt-% of the dishwashing detergent formulations, more preferably automatic dishwashing detergent formulations herein.

Preferred dishwashing detergent formulations, more preferably automatic dishwashing detergent formulations herein may additionally contain a dispersant polymer. When present, a dispersant polymer is typically at levels in the range from 0 wt-% to about 25 wt-%, preferably from about 0.5 wt-% to about 20 wt-%, more preferably from about 1 wt-% to about 8 wt-% of the detergent composition. Dispersant polymers are useful for improved filming performance of the present dishwasher detergent compositions, especially in higher pH embodiments, such as those in which wash pH exceeds about 9.5. Particularly preferred are polymers, which inhibit the deposition of calcium carbonate or magnesium silicate on dishware.

Suitable polymers are preferably at least partially neutralized or alkali metal, ammonium or substituted ammonium (e.g., mono-, di- or triethanolammonium) salts of polycarboxylic acids. The alkali metal, especially sodium salts are most preferred. While the molecular weight of the polymer can vary over a wide range, it preferably is from about 1,000 to about 500,000, more preferably is from about 1,000 to about 250,000.

Unsaturated monomeric acids that can be polymerized to form suitable dispersant polymers include acrylic acid, maleic acid (or maleic anhydride), fumaric acid, itaconic acid, aconitic acid, mesaconic acid, citraconic acid and methylenemalonic acid. The presence of monomeric segments containing no carboxylate radicals such as methyl vinyl ether, styrene, ethylene, etc. is suitable provided that such segments do not constitute more than about 50 wt-% of the dispersant polymer.

Copolymers of acrylamide and acrylate having a molecular weight of from about 3,000 to about 100,000, preferably from about 4,000 to about 20,000, and an acrylamide content of less than about 50 wt-%, preferably less than about 20 wt-% of the dispersant polymer can also be used. Most preferably, such dispersant polymer has a molecular weight of from about 4,000 to about 20,000 and an acrylamide content of from about 0 wt-% to about 15 wt-%, based on the total weight of the polymer.

Particularly preferred dispersant polymers are low molecular weight modified polyacrylate copolymers. Such copolymers contain as monomer units: a) from about 90 wt-% to about 10 wt-%, preferably from about 80 wt-% to about 20 wt-% acrylic acid or its salts and b) from about 10 wt-% to about 90 wt-%, preferably from about 20 wt-% to about 80 wt-% of a substituted acrylic monomer or its salt and have the general formula: —[(C(R$_a$)C(R$_b$)(C(O)OR$_c$)] wherein the apparently unfilled valencies are in fact occupied by hydrogen and at least one of the substituents R$_a$, R$_b$, or R$_c$, preferably R$_a$ or R$_b$, is a 1 to 4 carbon alkyl or hydroxyalkyl group; R$_a$ or R$_b$ can be a hydrogen and R$_c$ can be a hydrogen or alkali metal salt. Most preferred is a substituted acrylic monomer wherein R$_a$ is methyl, R$_b$ is hydrogen, and R$_c$ is sodium.

A suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized form of the polymer comprising about 70 wt-% acrylic acid and about 30 wt-% methacrylic acid.

Other dispersant polymers useful herein include the polyethylene glycols and polypropylene glycols having a molecular weight of from about 950 to about 30,000.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other suitable dispersant polymers are the carboxylated polysaccharides, particularly starches, celluloses and alginates.

Yet another group of acceptable dispersants are the organic dispersant polymers, such as polyaspartate.

Depending on whether a greater or lesser degree of compactness is required, filler materials can also be present in the instant dishwashing detergent formulations, more preferably automatic dishwashing detergent formulations. These include sucrose, sucrose esters, sodium sulfate, potassium sulfate, etc., in amounts up to about 70 wt-%, preferably from 0.1 wt-% to about 40 wt-% of the dishwashing detergent formulations, more preferably automatic dishwashing detergent formulations. Preferred filler is sodium sulfate, especially in good grades having at most low levels of trace impurities.

Sodium sulfate used herein preferably has a purity sufficient to ensure it is non-reactive with bleach; it may also be treated with low levels of sequestrants, such as phosphonates or EDDS in magnesium-salt form. Note that preferences, in terms of purity sufficient to avoid decomposing bleach, applies also to pH-adjusting component ingredients, specifically including any silicates used herein.

Organic solvents that can be used in the cleaning formulations according to the invention, especially when the latter are in liquid or paste form, include alcohols having from 1 to 4 carbon atoms, especially methanol, ethanol, isopropanol and tert-butanol, diols having from 2 to 4 carbon atoms, especially ethylene glycol and propylene glycol, and mixtures thereof, and the ethers derivable from the mentioned classes of compound. Such water-miscible solvents are present in the cleaning formulations according to the invention preferably in amounts not exceeding 20 wt-%, especially in amounts of from 1 wt-% to 15 wt-%.

Many dishwashing detergent formulations, more preferably automatic dishwashing detergent formulations herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH-jump systems, dual compartment containers, etc., and are well known to those skilled in the art.

Certain dishwashing detergent formulations, more preferably automatic dishwashing detergent formulations, comprise a pH-adjusting component selected from water-soluble alkaline inorganic salts and water-soluble organic or inorganic builders. The pH-adjusting components are selected so that when the dishwashing detergent formulation, more preferably automatic dishwashing detergent formulation is dissolved in water at a concentration of 1,000-5,000 ppm, the pH remains in the range of above about 8, preferably from about 9.5 to about 11. The preferred nonphosphate pH-adjusting component can be selected from the group consisting of:
(i) sodium carbonate or sesquicarbonate;
(ii) sodium silicate, preferably hydrous sodium silicate having $SiO_2:Na_2O$ ratio of from about 1:1 to about 2:1, and mixtures thereof with limited quantities of sodium metasilicate;
(iii) sodium citrate;
(iv) citric acid;
(v) sodium bicarbonate;
(vi) sodium borate, preferably borax;
(vii) sodium hydroxide; and
(viii) mixtures of (i)-(vii).

Preferred embodiments contain low levels of silicate (i.e. from about 3 wt-% to about 10 wt-% $SiO_2$).

Illustrative of highly preferred pH-adjusting component systems of this specialized type are binary mixtures of granular sodium citrate with anhydrous sodium carbonate, and three-component mixtures of granular sodium citrate trihydrate, citric acid monohydrate and anhydrous sodium carbonate.

The amount of the pH adjusting component in compositions used for automatic dishwashing is preferably from about 1 wt-% to about 50 wt-% of the composition. In a preferred embodiment, the pH-adjusting component is present in the composition in an amount from about 5 wt-% to about 40 wt-%, preferably from about 10 wt-% to about 30 wt-%.

For compositions herein having a pH between about 9.5 and about 11 of the initial wash solution, particularly preferred automatic dishwashing detergent formulations embodiments comprise, by weight of the automatic dishwashing detergent formulations, from about 5 wt-% to about 40 wt-%, preferably from about 10 wt-% to about 30 wt-%, most preferably from about 15 wt-% to about 20 wt-%, of sodium citrate with from about 5 wt-% to about 30 wt-%, preferably from about 7 wt-% to about 25 wt-%, most preferably from about 8 wt-% to about 20 wt-% sodium carbonate.

The essential pH-adjusting system can be complemented (i.e. for improved sequestration in hard water) by other optional detergency builder salts selected from nonphosphate detergency builders known in the art, which include the various water-soluble, alkali metal, ammonium or substituted ammonium borates, hydroxysulfonates, polyacetates, and polycarboxylates. Preferred are the alkali metals, especially sodium, salts of such materials. Alternate water-soluble, non-phosphorus organic builders can be used for their sequestering properties. Examples of polyacetate and polycarboxylate builders are the sodium, potassium, lithium, ammonium and substituted ammonium salts of ethylenediamine tetraacetic acid; nitrilotriacetic acid, tartrate monosuccinic acid, tartrate disuccinic acid, oxydisuccinic acid, carboxymethoxysuccinic acid, mellitic acid, and sodium benzene polycarboxylate salts. Further biodegradable buildes are, for example, aminoacid acetates, such as Trilon M (BASF) and Dissolvine GL (AKZO), as well as asparaginic acid derivatives, such as Baypure CX.

The detergent formulations can take a variety of physical forms such as, for example, powder granules, tablets (tabs), gel and liquid. Examples thereof include, inter alia, conventional high-performance detergent powders, supercompact high-performance detergent powders and tabs. One important physical form is the so-called concentrated granular form, which is added to a washing machine.

Also of importance are so-called compact or supercompact detergents. In the field of detergent manufacture, there is a trend towards the production of such detergents that contain an increased amount of active substances. In order to minimize energy consumption during the washing procedure, compact or supercompact detergents need to act effectively at low washing temperatures, for example below 40° C., or even at room temperature (25° C.). Such detergents usually contain only small amounts of fillers or of substances, such as sodium sulfate or sodium chloride, required for detergent manufacture. The total amount of such substances is usually from 0 to 10 wt-%, especially from 0 to 5 wt-%, more especially from 0 to 1 wt-%, based on the total weight of the detergent formulation. Such (super)compact detergents usually have a bulk density of from 650 to 1000 g/l, especially from 700 to 1000 g/l and more especially from 750 to 1000 g/l.

The detergent formulations can also be in the form of tablets (tabs). The advantages of tabs reside in the ease of dispensing and convenience in handling. Tabs are the most compact form of solid detergent formulation and usually have a volumetric density of, for example, from 0.9 to 1.3 kg/litre. To achieve rapid dissolution, such tabs generally contain special dissolution aids:
  carbonate/hydrogen carbonate/citric acid as effervescents;
  disintegrators, such as cellulose, carboxymethyl cellulose or cross-linked poly(N-vinylpyrrolidone);
  rapidly dissolving materials, such as sodium (potassium) acetates, or sodium (potassium) citrates;
  rapidly dissolving, water-soluble, rigid coating agents, such as dicarboxylic acids.

The tabs may also comprise combinations of such dissolution aids.

The detergent formulation may also be in the form of an aqueous liquid containing from 5 wt-% to 50 wt-%, preferably from 10 wt-% to 35 wt-%, of water or in the form of a non-aqueous liquid containing no more than 5 wt-%, preferably from 0 wt-% to 1 wt-% of water. Non-aqueous liquid detergent formulations may comprise other solvents as carriers. Low molecular weight primary or secondary alcohols, for example methanol, ethanol, propanol and isopropanol, are suitable for that purpose. The solubilising surfactant used is preferably a monohydroxy alcohol but polyols, such as those containing from 2 to 6 carbon atoms and from 2 to 6 hydroxy groups (e.g., 1,3-propanediol, ethylene glycol, glycerol and 1,2-propanediol) can also be used. Such carriers are usually used in a total amount of from 5 wt-% to 90 wt-%, preferably from 10 wt-% to 50 wt-%, based on the total weight of the detergent formulation. The detergent formulations can also used in so-called "unit liquid dose" form.

Also an aspect of the invention is a granule comprising
a) from 1-99 wt-%, based on the total weight of the granule, of at least one compound of formula (1) as described above and of at least one peroxide,
b) from 1-99 wt-%, based on the total weight of the granule, of at least one binder,
c) from 0-20 wt-%, based on the total weight of the granule, of at least one encapsulating material,
d) from 0-20 wt-%, based on the total weight of the granule, of at least one further additive and
e) from 0-20 wt-% based on the total weight of the granule, of water.

The granules according to the invention comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain α-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinylpyrrolidone/dimethylaminoethyl methacrylates, copolymers of styrene and acrylic acid, polycarboxylic acids, polyacrylamides, carboxymethyl cellulose, hydroxymethyl cellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxymethyl cellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolymers of ethyl acrylate with methacrylate and methacrylic acid, and polymathacrylates.

Encapsulating materials include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents. Examples have already been given above.

Another aspect of the invention is a process for the bleaching of stains or of soiling on textile materials in the context of a washing process or by the direct application of a stain remover and for the cleaning of hard surfaces comprising bringing into contact a textile material or a hard surface material in an aqueous medium, a compound of formula (1) as described above and a peroxide or a peroxide-precursor or $O_2$ and/or air.

Yet another aspect of the invention is the use, as a catalyst for oxidation reactions, of at least one compound of formula (1)

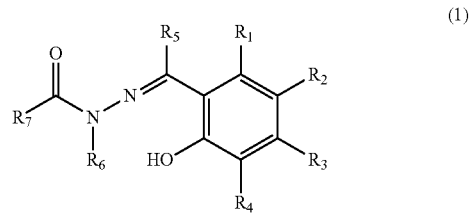

wherein
$R_1$, $R_2$, $R_3$, $R_4$ independently from each other are hydrogen, unsubstituted or substituted $C_1$-$C_{28}$alkyl, $C_1$-$C_{28}$alkoxy, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or napththyl, wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy;
or $R_1$, $R_2$, $R_3$, $R_4$ independently from each other are $OR_{11}$, $NR_{11}R_{12}$, $NO_2$ or halogen; or
$R_1$ and $R_2$, $R_2$ and $R_3$ or $R_3$ and $R_4$ are linked together to form 1, 2 or 3 carbocyclic or heterocyclic rings, which may be uninterrupted or interrupted by one or more —O—, —S— or —$NR_{13}$— and or which may be further fused with other aromatic rings and/or which may be substituted with one or more $C_1$-$C_6$akyl groups.
$R_5$ denotes hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy;
$R_6$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphtyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy or naphthyloxy;
$R_7$ is a group

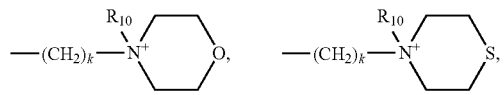

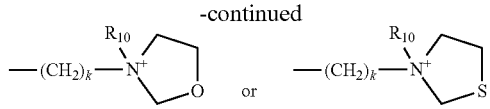

each group with an anion $A^-$;

k is an integer from 1 to 4;

$A^-$ is an anion;

$R_{10}$ denotes hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl;

$R_{11}$, $R_{12}$ independently are hydrogen, $C_1$-$C_{18}$alkyl or phenyl; or $R_{11}$ and $R_{12}$ together with the nitrogen atom to which they are bonded form a 5 or 6 membered-ring which may contain a further N, O or S atom.

$R_{13}$ denotes hydrogen or $C_1$-$C_{18}$alkyl.

Preferably the compounds of formula (1) are used as catalysts together with peroxide or a peroxide-precursor, $O_2$ and/or air for the bleaching of stains or of soiling on textile materials in the context of a washing process or by the direct application of a stain remover; for the cleaning of hard surfaces.

In a specific embodiment an additional bleach activator is used together with the compound of formula (1) and a peroxide or a peroxide-precursor, $O_2$ and/or air.

In another specific embodiment a metal chelating agent (sequestrant) is used present together with the compound of formula (1) and a peroxide or a peroxide-precursor, $O_2$ and/or air.

In many cases the bleach activator and the metal chelating agent (sequestrant) are used together with the compound of formula (1) and a peroxide or a peroxide-precursor, $O_2$ and/or air.

Definitions and preferences given above apply equally for all aspects of the invention.

The following examples illustrate the invention.

A) SYNTHESIS EXAMPLES

Example A1

Compound 1A, Precursor

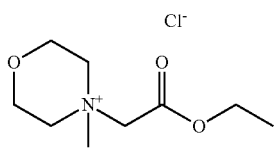

ethyl 2-(4-methylmorpholin-4-ium-4-yl)acetate chloride

The title compound is synthesized as described in U.S. Pat. No. 3,398,147.

$^1$H-NMR (300 MHz, DMSO), δ [ppm]: 1.25 (t, J=7.2 Hz, 3H), 3.41 (s, 3H), 3.62-3.79 (m, 4H), 3.96-3.99 (m, 4H), 4.24 (q, J=7.2 Hz, 2H), 4.806 (s, 2H).

Compound 101.

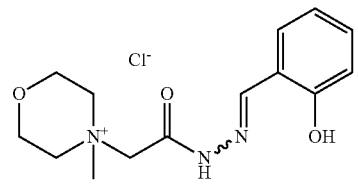 [SMILES: C[N+]1(CC(=O)NN=Cc2ccccc2O)CCOCC1 ; [Cl-]]

N-[(2-hydroxyphenyl)methyleneamino]-2-(4-methylmorpholin-4-ium-4-yl)acetamide chloride 20.1 g (0.09 mol) of compound 1A are dissolved in 100 ml Ethanol. 9.1 g (0.18 mol) of hydrazine monohydrate are added drop wise at room temperature. A white suspension is obtained at the end of the addition and the reaction mixture is stirred at room temperature for 3 hours. The solid is then quickly filtrated and dried. It is then further suspended in 100 ml ethanol and 11.2 g (0.09 mol) of salicylaldehyde are added drop wise at room temperature. The reaction mixture is stirred at room temperature for 19 hours and is then filtrated. The white solid obtained is dried to give 23.1 g of a mixture of two isomers of compound 101.

$^1$H-NMR (300 MHz, DMSO), δ [ppm]: 3.45 (broad s, 3H), 3.60-3.87 (m, 4H), 3.93-4.07 (m, 4H), 4.63 and 4.95 (2 s, 1H), 6.83-7.02 (m, 2H), 7.23-7.33 (m, 1H), 7.60 and 7.79 (2 dd, $J_1$=1.5 Hz, $J_2$=7.8 Hz and $J_1$=1.8 Hz, $J_2$=8.1 Hz, 1H), 8.42 and 8.64 (2s, 1H), 10.31 and 10.85 (2s, 1H), 12.03 and 13.36 (2s, 1H).

Example A2

Compound 1B, Precursor

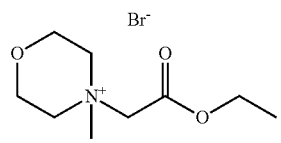

ethyl 2-(4-methylmorpholin-4-ium-4-yl)acetate bromide

The title compound was synthesized as described in Koumoto, Kazuya; Ochiai, Hirofumi; Sugimoto, Naoki Tetrahedron 2007, 64, 168.

$^1$H-NMR (300 MHz, DMSO), δ [ppm]: 1.25 (t, J=7.2 Hz, 3H), 3.40 (s, 3H), 3.60-3.77 (m, 4H), 3.91-4.04 (m, 4H), 4.26 (q, J=7.2 Hz, 2H), 4.74 (s, 2H).

Compound 1C, Precursor

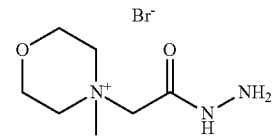

2-(4-methylmorpholin-4-ium-4-yl)acetohydrazide bromide 24.1 g (0.09 mol) of compound 1B are stirred with 100 ml ethanol. 7.7 g (0.15 mol) of hydrazine monohydrate are added drop wise at room temperature. 5 min after the end of the addition, a white solid starts precipitating. The reaction mixture is stirred at room temperature for 5 hours. The solid is then quickly filtrated and dried to give 18.2 g of compound 1C.

$^1$H-NMR (300 MHz, DMSO), δ [ppm]: 3.33 (s, 3H), 3.53-3.69 (m, 4H), 3.91-4.00 (m, 4H), 4.21 (s, 2H), 4.54-4.63 (m, 2H), 9.78 (s broad, 1H).

Compound 101B.

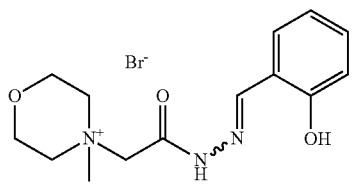 [SMILES: C[N+]1(CC(=O)NN=Cc2ccccc2O)CCOCC1 ; [Br-]]

N-[(2-hydroxyphenyl)methyleneamino]-2-(4-methylmorpholin-4-ium-4-yl)acetamide bromide 17.8 g (0.07 mol) of compound 1C are stirred with 100 ml ethanol. 8.7 g (0.07 mol) of salicylaldehyde were added drop wise at room temperature. A thick white suspension is obtained and is stirred at room temperature overnight. The solid is then filtrated and dried to give 23.4 g of a white solid: a mixture of two isomers of compound 101B.

$^1$H-NMR (300 MHz, DMSO), δ [ppm]: 3.45 (s, 3H), 3.64-3.87 (m, 4H), 3.94-4.06 (m, 4H), 4.54 and 4.95 (2 s, 1H), 6.85-6.95 (m, 2H), 7.25-7.34 (m, 1H), 7.62 and 7.80 (2 dd, $J_1$=1.5 Hz, $J_2$=7.8 Hz and $J_1$=1.5 Hz, $J_2$=7.8 Hz, 1H), 8.39 and 8.56 (2s, 1H), 10.08 and 10.75 (broad 2s, 1H), 11.95 and 12.51 (broad 2s, 1H).

Compound 102

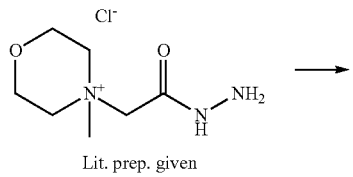

Lit. prep. given

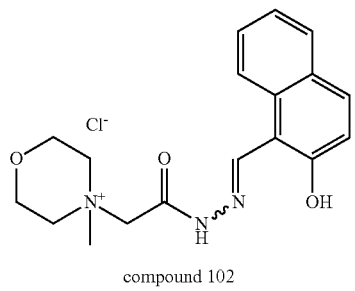

compound 102

N-(2-hydroxy-1-naphthyl)methyleneamino]-2-(4-methylmorpholin-4-ium-4-yl)acetamide chloride 2-hydroxynaphthaldehyde (98%; 5.08 g, 0.0289 mol) is added at 25° C. to a stirred suspension of 2-(4-methylmorpholin-4-ium-4-yl)acetohydrazide chloride (5.77 g, 0.0275 mol; prepared according to U.S. Pat. No. 3,398,147) in ethanol (50 ml) and the resulting suspension subsequently stirred at 25° C. (overnight) and 50° C. (one hour). The reaction mixture is filtered, the filter cake re-suspended in fresh ethanol (70 ml) and the resulting suspension refluxed (one hour). Warm (45° C.) filtration and drying of the filter cake affords the title compound (7.1 g). Yellow beige solid;

$^1$H-NMR (400 MHz, DMSO-d$_6$), δ [ppm]: 3.48 (s) and 3.50 (s; 3H), 3.65-3.88 (m, 4H), 3.97-4.08 (m, 4H), 4.62 (s) and 5.03 (s; 2H), 7.25-7.27 (m, d-like) and 7.31-7.33 (m, d-like; 1H), 7.37-7.43 (m, 1H), 7.57-7.62 (m, 1H), 7.85-7.87 (m, d-like), 7.89-7.91 (m, d-like) and 7.94-7.96 (m, d-like; 2H), 8.41-8.43 (m, d-like) and 8.80-8.82 (m, d-like; 1H), 8.96 (s) and 9.47 (s; 1H), 10.84 (broad s), 12.07 (broad s), 12.16 (broad s) and 13.54 (broad s; 2H);

LC/MS (pos. ESI), area % (m/z): found 98.6 (328.2). calcd. for $C_{18}H_{22}N_3O_3$: 328.

Elemental analysis (Cl only): found 9.4%. calcd. for $C_{18}ClH_{22}N_3O_3$: 9.7%.

Compound 103

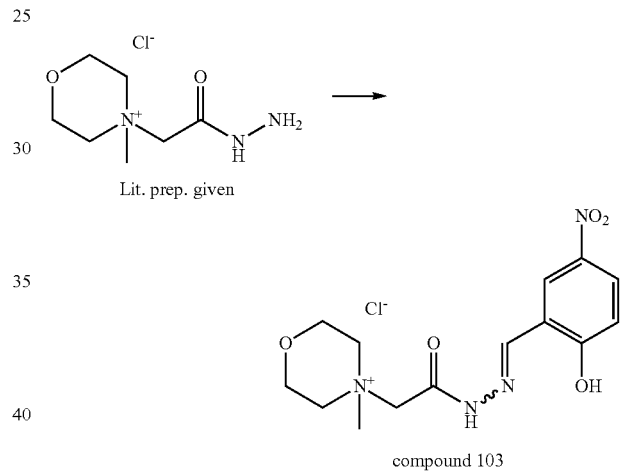

compound 103

N-(2-hydroxy-5-nitro-phenyl)methyleneamino]-2-(4-methylmorpholin-4-ium-4-yl)acetamide chloride 2-Hydroxy-5-nitrobenzaldehyde (99%; 5.0 g, 0.0296 mol) is added at 25° C. to a stirred suspension of 2-(4-methylmorpholin-4-ium-4-yl)acetohydrazide chloride (5.91 g, 0.0282 mol; prepared according to U.S. Pat. No. 3,398,147) in ethanol (50 ml) and the resulting suspension subsequently stirred at 25° C. (overnight) and 5° C. (15 minutes). The reaction mixture is filtered and the filter cake dried to afford the title compound (9.9 g). Beige solid;

$^1$H-NMR (400 MHz, DMSO-d$_6$), δ [ppm]: 3.45 (s, 3H), 3.62-3.85 (m, 4H), 3.95-4.06 (m, 4H), 4.59 (s) and 5.01 (s; 2H), 7.21 (d, J=9.1 Hz) and 7.26 (d, J=9.1 Hz; 1H), 8.19 (dd, J=9.1 and 2.9 Hz, 1H), 8.42 (s), 8.57 (d, J=2.9 Hz), 8.59 (d, J=2.9 Hz) and 8.67 (s; 2H), 12.11 (broad s), 12.19 (broad s) and 13.26 (broad s; 2H);

LC/MS (pos. ESI), area % (m/z): found 99.0 (323.2). calcd. for $C_{14}H_{19}N_4O_5$: 323.

Elemental analysis (Cl only): found 9.5%. calcd. for $C_{14}ClH_{19}N_4O_5$: 9.9%.

Compound 104

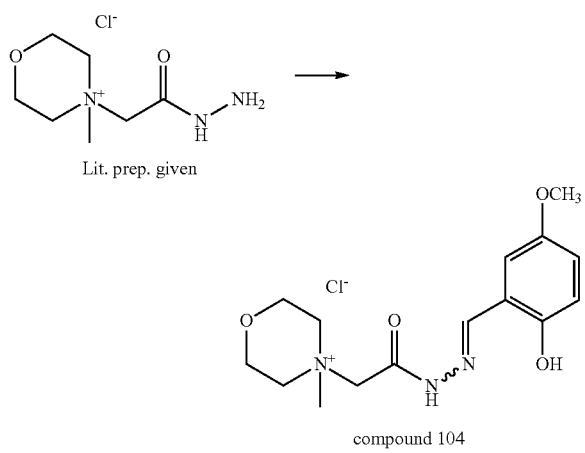

compound 104

N-(2-hydroxy-5-methoxy-phenyl)methyleneamino]-2-(4-methylmorpholin-4-ium-4-yl)acetamide chloride 2-Hydroxy-5-methoxybenzaldehyde (98%; 4.74 g, 0.0305 mol) is added via syringe within two minutes at 25° C. to a stirred suspension of 2-(4-methylmorpholin-4-ium-4-yl)acetohydrazide chloride (6.1 g, 0.0291 mol; prepared according to U.S. Pat. No. 3,398,147) in ethanol (50 ml), resulting in the formation of a voluminous precipitate. The reaction mixture is diluted with ethanol (20 ml) and subsequently stirred at 50° C. (one hour) and 25° C. (overnight). Filtration and drying of the filter cake affords the title compound (9.38 g). Yellowish solid;

$^1$H-NMR (400 MHz, DMSO-d$_6$), δ [ppm]: 3.44 (s, 3H), 3.61-3.62 (m, 1H), 3.69-3.74 (m, 2H), 3.72 (s) and 3.73 (s; 3H), 3.79-3.85 (m, 1H), 3.95-4.05 (m, 4H), 4.58 (broad s) and 4.95 (s; 2H), 6.88-6.94 (m, 2H), 7.15-7.16 (m, d-like) and 7.305-7.310 (m, d-like; 1H), 8.37 (s) and 8.59 (s; 1H), 9.78-9.79 (m, d-like), 10.31 (s), 12.00 (s) and 13.08-13.13 (m, d-like; 2H);

LC/MS (pos. ESI), area % (m/z): found 100.0 (308.2). calcd. for C$_{15}$H$_{22}$N$_3$O$_4$: 308.

Elemental analysis (Cl only): found 10.1%. calcd. for C$_{15}$ClH$_{22}$N$_3$O$_4$: 10.3%.

Compound 105

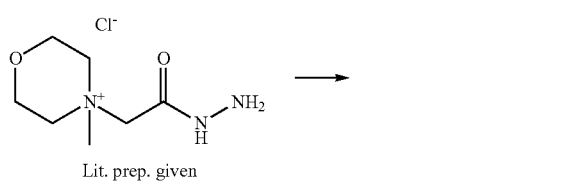

compound 105

N-(2-hydroxy-3-nitro-phenyl)methyleneamino]-2-(4-methylmorpholin-4-ium-4-yl)acetamide chloride 2-Hydroxy-3-nitrobenzaldehyde (98%; 4.9 g, 0.0287 mol) is added at 25° C. to a stirred suspension of 2-(4-methylmorpholin-4-ium-4-yl)acetohydrazide chloride (5.73 g, 0.0273 mol; prepared according to U.S. Pat. No. 3,398,147) in ethanol (50 ml). The reaction mixture is brought to 50° C., diluted with ethanol (20 ml), stirred for two hours at 50° C., cooled to 10° C. and filtered. The filter cake is dissolved in refluxing methanol (400 ml), filtered and the clear hot filtrate allowed to cool down. The resulting precipitate is separated off and dried to afford the title compound (7.8 g). Yellow solid;

$^1$H-NMR (400 MHz, DMSO-d$_6$), δ [ppm]: 3.36 (broad s, 1H), 3.45 (s) and 3.46 (s; 3H), 3.62-3.68 (m, 1H), 3.70-3.76 (m, 2H), 3.80-3.86 (m, 1H), 3.95-4.05 (m, 4H), 4.66 (s) and 5.00 (s; 2H), 7.12-7.18 (m, q-like, 1H), 7.97-8.00 (m, dd-like), 8.02-8.05 (m, dd-like), 8.07-8.09 (m, dd-like) and 8.20-8.22 (m, dd-like; 2H), 8.50 (s) and 8.74 (s; 1H), 12.29 (s, 1H);

LC/MS (pos. ESI), area % (m/z): found 100.0 (323.2). calcd. for C$_{14}$H$_{19}$N$_4$O$_5$: 323.

Elemental analysis (Cl only): found 9.0%. calcd. for C$_{14}$ClH$_{19}$N$_4$O$_5$: 9.9%.

Compound 107 (Comparison).

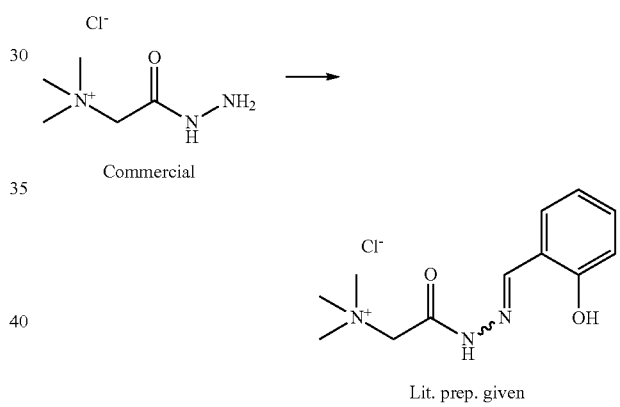

[2-[[(2-hydroxyphenyl)methylene]hydrazino]-2-oxo-ethyl]-trimethyl-ammonium chloride From commercially available (2-hydrazino-2-oxo-ethyl)-trimethyl-ammonium chloride (Girard-T reagent) and salicylaldehyde in ethanol according to the procedure published by V. Leovac et al., *Structural Chemistry* 2007, 18, 113-119.

B) APPLICATION EXAMPLES (PHOSPHATE CONTAINING DETERGENT)

Application Example B1

Peroxide Bleaching Action in Washing Agents 50 g of white cotton fabric and 0.5 g each BC01, BC03 (tea stain), BC02 (coffee stain), CS12 (red currant stain) on cotton fabric are treated in 250 ml of washing liquor. The liquor contains ECE77 (phosphate builder) standard detergent in a concentration of 4.5 g/l, and 0.92 g/l sodium percarbonate (SPC), 0.176 mg TAED, pH adjusted to pH 10.1. The catalyst concentration is 25 μmol/l. The washing process is carried out in a steel beaker in a LINITEST apparatus for 60 minutes at 30° C. For evaluating the bleaching results, the increase in the lightness DY (difference in lightness according to CIE) of the stains brought about by the treatment is determined spectrophotometrically The higher the ΔY value, the better the bleach performance

|  | BC01 | BC02 | BC03 | CS12 |  |
| --- | --- | --- | --- | --- | --- |
| No catalyst | 10.4 | 9.4 | 10.8 | 49 | Reference |
| Compound 101A | 15.5 | 12.9 | 18.3 | 51.1 | Invention |
| Compound 107 | 11.9 | 9.8 | 14.2 | 49.5 | Comparison |

The results clearly show that compound 101A according to the invention exhibits a significantly higher lightness as compared to the reference compound.

Odor of the Wash Liquors

After the washing experiment the wash liquor containing compound 101A has no scent.

The wash liquor containing the comparative compound 107 exhibits a clear fishy smell, which is highly undesired.

Application Example B2

Peroxide Bleaching, Influence of Sequestrants 50 g of white cotton fabric and 0.5 g each BC01, BC03 (tea stain), BC02 (coffee stain), CS12 (red currant stain) on cotton fabric are treated in 250 ml of washing liquor. The liquor contains AATCC standard detergent in a concentration of 4.5 g/l, and 0.65 g/l sodium percarbonate (SPC), 144 mg TAED, pH adjusted to pH 10.1, tap water. The catalyst concentration is 35 μmol/l. The experiments are carried out with 1% active material on weight of detergent of different sequestrants with and without catalyst. Sequestrants used are: citric acid, oxalic acid, methyl-glycine-diacetic acid (MGDA), ethylenediamine-N,N'-disuccinic acid (EDDS), 1-hydroxy ethylidene-1,1-diphosphonic acid (HEDP).

The washing process is carried out in a steel beaker in a LINITEST apparatus for 60 minutes at 30° C. For evaluating the bleaching results, the increase in the lightness ΔY (difference in lightness according to CIE) of the stains brought about by the treatment is determined spectrophotometrically. The higher the ΔY value, the better the bleach performance.

|  | BC01 | BC02 | BC03 | CS12 |
| --- | --- | --- | --- | --- |
| TAED Reference | 9.0 | 7.7 | 8.7 | 44.3 |
| + EDDS | 8.0 | 6.9 | 6.9 | 42.9 |
| + MGDA | 8.4 | 7.3 | 7.8 | 42.9 |
| + Oxalic acid | 8.5 | 7 | 8.2 | 43.3 |

-continued

|  | BC01 | BC02 | BC03 | CS12 |
| --- | --- | --- | --- | --- |
| + Citic acid | 8.4 | 7.2 | 7.9 | 42.5 |
| + HEDP | 8.5 | 7.2 | 7.6 | 46.2 |
| + Comp. 101A | 13.2 | 9.5 | 14.6 | 43.5 |
| + Comp. 101A + EDDS | 15.2 | 11.6 | 18.2 | 49.2 |
| + Comp. 101A + MGDA | 15.2 | 10.7 | 18.7 | 47.9 |
| + Comp. 101A + Oxalic acid | 14.0 | 9.6 | 15.5 | 44.5 |
| + Comp. 101A + Citric acid | 14.9 | 10.3 | 17.0 | 46.5 |
| + Comp. 101A + HEDP | 15.1 | 11.3 | 17.7 | 47.6 |

The results clearly show a synergistic effect of the combination of Comp. 101+sequestrant.

Application Example B3

Peroxide Bleaching, Performance without TAED 50 g of white cotton fabric and 0.5 g each BC01, BC03 (tea stain), BC02 (coffee stain), CS12 (red currant stain) on cotton fabric are treated in 250 ml of washing liquor. The liquor contains AATCC standard detergent in a concentration of 4.3 g/l, and 0.43 g/l sodium percarbonate (SPC), 43 mg HEDP, pH 10.1, tap water. The concentration of Comp. 101 is varied from 7.5-25 μM.

Reference 1 contains SPC only, Reference 2 contains SPC+32 mg TAED.

The washing process is carried out in a steel beaker in a LINITEST apparatus for 60 minutes at 40° C. For evaluating the bleaching results, the increase in the lightness ΔY (difference in lightness according to CIE) of the stains brought about by the treatment is determined spectrophotometrically. The higher the ΔY value, the better the bleach performance.

| | BC01 | BC02 | BC03 | CS12 |
|---|---|---|---|---|
| Ref. 1 - Det + SPC | 9.1 | 5.9 | 9.2 | 43.3 |
| Ref. 2 - Det + SPC + TAED | 9.6 | 7.1 | 11.3 | 46.2 |
| Det + SPC + 7.5 µM Comp. 101A | 10.4 | 7.2 | 11.6 | 46.5 |
| Det + SPC + 10 µM Comp. 101A | 10.8 | 7.5 | 12.1 | 47.2 |
| Det + SPC + 15 µM Comp. 101A | 10.9 | 8.2 | 13.2 | 47.9 |
| Det + SPC + 20 µM Comp. 101A | 11.6 | 8.6 | 14.2 | 48.3 |
| Det + SPC + 25 µM Comp. 101A | 12.0 | 8.9 | 13.7 | 48.9 |

The results show that Comp. 101A catalyzes the peroxide bleach and is easily able to exceed the state of the art bleach system SPC/TAED.

Application Example B4, Other Compounds

Peroxide Bleaching, Performance with TAED 50 g of white cotton fabric and 0.5 g each BC01, BC03 (tea stain), BC02 (coffee stain), CS12 (red currant stain) on cotton fabric are treated in 250 ml of washing liquor. The liquor contains AATCC standard detergent in a concentration of 4.7 g/l, and 0.66 g/l sodium percarbonate (SPC), 144 mg/l TAED, 43 mg HEDP, pH 10.1, tap water. The concentration of the different compounds is 20 µmol/l.

Reference contains SPC+TAED as bleach system.

The washing process is carried out in a steel beaker in a LINITEST apparatus for 60 minutes at 30° C. For evaluating the bleaching results, the increase in the lightness ΔY (difference in lightness according to CIE) of the stains brought about by the treatment is determined spectrophotometrically. The higher the ΔY value, the better the bleach performance.

| | BC01 | BC02 | BC03 | CS12 |
|---|---|---|---|---|
| Reference | 8.5 | 6.9 | 9.0 | 46.0 |
| Reference + Comp. 102 | 12.1 | 8.8 | 15.1 | 47.0 |
| Reference + Comp. 103 | 10.2 | 7.5 | 10.6 | 47.1 |
| Reference + Comp. 104 | 10.0 | 7.1 | 10.1 | 45.9 |
| Reference + Comp. 105 | 9.6 | 7.0 | 10.6 | 48.2 |

Application Example B5, Other Compounds

Peroxide Bleaching, Performance without TAED 50 g of white cotton fabric and 0.5 g each BC01, BC03 (tea stain), BC02 (coffee stain), CS12 (red currant stain) on cotton fabric are treated in 250 ml of washing liquor. The liquor contains EU base detergent in a concentration of 4.7 g/l, and 0.66 g/l sodium percarbonate (SPC), 43 mg HEDP, pH 10.2, tap water. The concentration of the different compounds is 20 µmol/l.

Reference contains SPC as bleach system.

The washing process is carried out in a steel beaker in a LINITEST apparatus for 60 minutes at 40° C. For evaluating the bleaching results, the increase in the lightness ΔY (difference in lightness according to CIE) of the stains brought about by the treatment is determined spectrophotometrically. The higher the ΔY value, the better the bleach performance.

| | BC01 | BC02 | BC03 | CS12 |
|---|---|---|---|---|
| Reference | 8.1 | 6.1 | 8.2 | 43.4 |
| Reference + Comp. 102 | 11.7 | 8.9 | 15.4 | 47.8 |
| Reference + Comp. 104 | 10.7 | 7.8 | 12.8 | 46.1 |

The invention claimed is:

1. A method of oxidizing a compound comprising contacting the compound with a catalyst for oxidation reactions wherein the catalyst is at least one compound of formula (1)

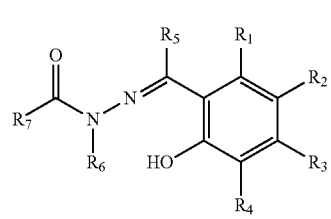

wherein
$R_1$, $R_2$, $R_3$, $R_4$ independently from each other are hydrogen, unsubstituted or substituted $C_1$-$C_{28}$alkyl, $C_1$-$C_{28}$alkoxy, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;
or $R_1$, $R_2$, $R_3$, $R_4$ independently from each other are $OR_{11}$, $NR_{11}R_{12}$, $NO_2$ or halogen;
or
$R_1$ and $R_2$, $R_2$ and $R_3$ or $R_3$ and $R_4$ are linked together to form 1, 2 or 3 carbocyclic or heterocyclic rings, which may be uninterrupted or interrupted by one or more —O—, —S— or —$NR_{13}$— and or which may be further fused with other aromatic rings and/or which may be substituted with one or more $C_1$-$C_6$akyl groups;
$R_5$ is hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;
$R_6$ is hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;

$R_7$ is a group

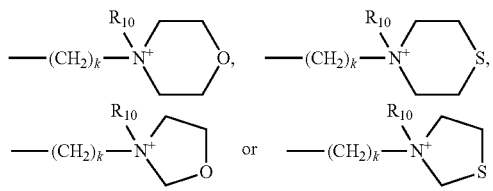

each group with an anion $A^-$;
k is an integer from 1 to 4;
$A^-$ is an anion;
$R_{10}$ is hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl;
$R_{11}$, $R_{12}$ independently are hydrogen, $C_1$-$C_{15}$alkyl or phenyl; or $R_{11}$ and $R_{12}$ together with the nitrogen atom to which they are bonded form a 5 or 6 membered-ring which may contain a further N, O or S atom; and
$R_{13}$ is hydrogen or $C_1$-$C_{18}$alkyl,
together with a peroxide or a peroxide precursor.

2. The method according to claim 1 wherein the at least one compound of formula (1) is further used as catalysts together with $O_2$ and/or air.

3. The method according to claim 1 wherein a bleach activator is present.

4. The method according to claim 1 wherein additionally a metal chelating agent is present.

5. The method according to claim 2 for oxidizing of stains or soiling on textile materials in a washing process or by the direct application of a stain remover or for the cleaning of hard surfaces.

6. The method according to claim 5 wherein a bleach activator is present.

7. The method according to claim 5 wherein additionally a metal chelating agent is present.

8. The method according to claim 6 wherein additionally a metal chelating agent is present.

9. The method of claim 1 wherein, in the compound of formula (1),
$R_1$, $R_2$, $R_3$, $R_4$ independently from each other are hydrogen, $C_1$-$C_8$ alkyl, $C_1$-$C_8$alkoxy, halogen, $OR_{11}$ or $NR_{11}R_{12}$;
$R_5$ is hydrogen or $C_1$-$C_{18}$alkyl;
$R_6$ is hydrogen or $C_1$-$C_{18}$alkyl;
$R_7$ is a group

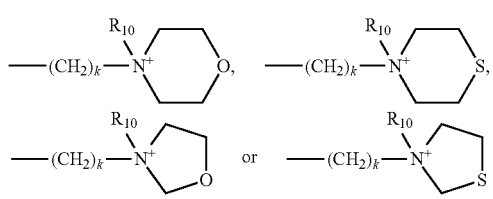

each group with an anion $A^-$;
k is an integer from 1 to 4;
$A^-$ is $Cl^-$, $Br^-$, $ClO_4^-$, $NO_3^-$, $HSO_4^-$, $BF_4^-$ or $PF_6^-$;
$R_{10}$ is hydrogen or $C_1$-$C_{18}$alkyl;
$R_{11}$, $R_{12}$ independently are hydrogen, $C_1$-$C_{18}$alkyl or phenyl; and
$R_{13}$ is hydrogen or $C_1$-$C_4$alkyl.

10. The method of claim 1 wherein, in the compound of formula (1),
$R_1$, $R_2$, $R_3$, $R_4$ independently from each other are hydrogen, OH, methoxy, halogen or methyl;
$R_5$ is hydrogen or methyl;
$R_6$ is hydrogen or methyl;
$R_7$ is a group

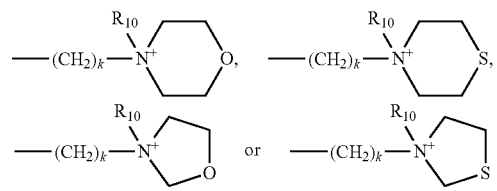

each group with an anion $A^-$;
k is an integer from 1 to 2;
$A^-$ is $Cl^-$, $Br^-$, $ClO_4^-$, $NO_3^-$, $HSO_4^-$, $BF_4^-$ or $PF_6^-$; and
$R_{10}$ is hydrogen or $C_1$-$C_4$alkyl.

11. The method of claim 1 wherein, in the compound of formula (1),
$R_1$, $R_2$, $R_3$, $R_4$ independently from each other are hydrogen, OH, or methyl;
$R_5$ is hydrogen;
$R_6$ is hydrogen;
$R_7$ is a group

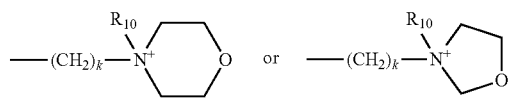

each group with an anion $A^-$;
k is 1;
$A^-$ is $Cl^-$, $Br^-$, $ClO_4^-$, $NO_3^-$, $HSO_4^-$, $BF_4^-$ or $PF_6^-$; and
$R_{10}$ is methyl.

12. The method of claim 1 wherein, in the compound of formula (1),
$R_1$, $R_2$, $R_3$, $R_4$ are hydrogen;
$R_5$ is hydrogen;
$R_6$ is hydrogen;
$R_7$ is a group

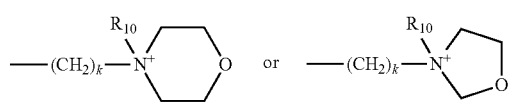

each group with an anion $A^-$;
k is 1;
$A^-$ is $Cl^-$ or $Br^-$; and
$R_{10}$ is methyl.

13. A method of oxidizing a compound comprising contacting the compound with a catalyst for oxidation reactions wherein the catalyst is at least one compound of formula (1)

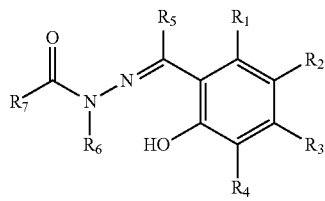

(1)

wherein $R_1$, $R_2$, $R_3$, $R_4$ independently from each other are hydrogen, unsubstituted or substituted $C_1$-$C_{28}$alkyl, $C_1$-$C_{28}$alkoxy, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;

or $R_1$, $R_2$, $R_3$, $R_4$ independently from each other are $OR_{11}$, $NR_{11}R_{12}$, $NO_2$ or halogen;

or $R_1$ and $R_2$, $R_2$ and $R_3$ or $R_3$ and $R_4$ are linked together to form 1, 2 or 3 carbocyclic or heterocyclic rings, which may be uninterrupted or interrupted by one or more —O—, —S— or —$NR_{13}$— and or which may be further fused with other aromatic rings and/or which may be substituted with one or more $C_1$-$C_6$akyl groups;

$R_5$ is hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;

$R_6$ is hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$mheteroaralkyl, unsubstituted or substituted phenyl or naphthyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;

$R_7$ is a group

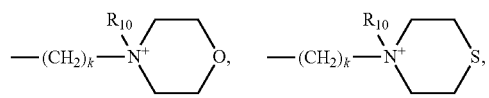

-continued

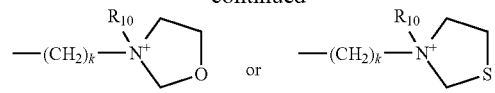

each group with an anion $A^-$;

k is an integer from 1 to 4;

$A^-$ is an anion;

$R_{10}$ is hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl;

$R_{11}$, $R_{12}$ independently are hydrogen, $C_1$-$C_{18}$alkyl or phenyl; or $R_{11}$ and $R_{12}$ together with the nitrogen atom to which they are bonded form a 5 or 6 membered-ring which may contain a further N, O or S atom; and $R_{13}$ is hydrogen or $C_1$-$C_{18}$alkyl, together with a bleach activator.

14. The method according to claim 13, wherein additionally a metal chelating agent is present.

15. A method of oxidizing a compound comprising contacting the compound with a catalyst for oxidation reactions wherein the catalyst is at least one compound of formula (1)

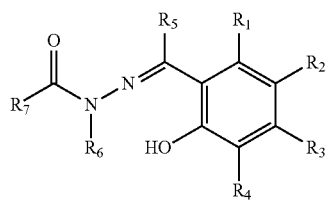

(1)

wherein $R_1$, $R_2$, $R_3$, $R_4$ independently from each other are hydrogen, unsubstituted or substituted $C_1$-$C_{28}$alkyl, $C_1$-$C_{28}$alkoxy, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;

or $R_1$, $R_2$, $R_3$, $R_4$ independently from each other are $OR_{11}$, $NR_{11}R_{12}$, $NO_2$ or halogen;

or $R_1$ and $R_2$, $R_2$ and $R_3$ or $R_3$ and $R_4$ are linked together to form 1, 2 or 3 carbocyclic or heterocyclic rings, which may be uninterrupted or interrupted by one or more —O—, —S— or —$NR_{13}$— and or which may be further fused with other aromatic rings and/or which may be substituted with one or more $C_1$-$C_6$akyl groups;

$R_5$ is hydrogen, unsubstituted or substituted $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino;

N-naphthylamino wherein the amino groups may be quaternised; phenyl; phenoxy and naphthyloxy;

$R_6$ is hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl, unsubstituted or substituted phenyl or naphthyl, or unsubstituted or substituted heteroaryl; wherein the substituents for the radicals are selected from the group consisting of $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino wherein the amino groups may be quaternised; phenyl; phenoxy and naphthyloxy;

$R_7$ is a group

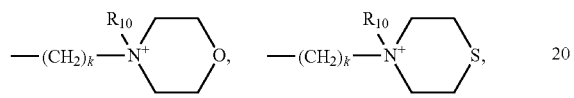

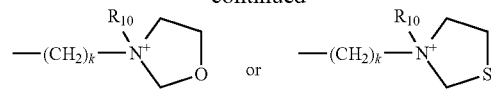

each group with an anion $A^-$;

k is an integer from 1 to 4;

$A^-$ is an anion;

$R_{10}$ is hydrogen, $C_1$-$C_{28}$alkyl, $C_2$-$C_{28}$alkenyl, $C_2$-$C_{22}$alkinyl, $C_3$-$C_{12}$cycloalkyl, $C_3$-$C_{12}$cycloalkenyl, $C_7$-$C_9$aralkyl, $C_3$-$C_{20}$heteroalkyl, $C_3$-$C_{12}$cycloheteroalkyl, $C_5$-$C_{16}$heteroaralkyl;

$R_{11}$, $R_{12}$ independently are hydrogen, $C_1$-$C_{18}$alkyl or phenyl; or $R_{11}$ and $R_{12}$ together with the nitrogen atom to which they are bonded form a 5 or 6 membered-ring which may contain a further N, O or S atom; and $R_{13}$ is hydrogen or $C_1$-$C_{18}$alkyl, together with a metal chelating agent.

* * * * *

UNITED STATES PATENT AND TRADEMARK OFFICE
CERTIFICATE OF CORRECTION

PATENT NO. : 9,533,296 B2
APPLICATION NO. : 15/005288
DATED : January 3, 2017
INVENTOR(S) : Hauke Rohwer et al.

It is certified that error appears in the above-identified patent and that said Letters Patent is hereby corrected as shown below:

On the Title Page

At item (62), Line 2, "2015," should be -- 2015, now Pat. No. 9,296,713, --.

In the Claims

At Column 33, Line 25, "$C_1$-$C_{15}$alkyl" should be -- $C_1$-$C_{18}$alkyl --.

At Column 33, Line 33, "$O_2$and/or" should be -- $O_2$ and/or --.

At Column 33, Line 38, "of stains" should be -- stains --.

At Column 33, Line 51, "$C_1$-$C_8$ alkyl," should be -- $C_1$-$C_8$alkyl, --.

At Column 35, Line 49, "$C_3$-$C_{12}$cycloalkenyl," should be -- $C_3$-$C_{12}$cycloalkenyl, --.

At Column 35, Lines 50-51, "$C_3$-$C_{12}$cycloheteroalkyl," should be -- $C_3$-$C_{12}$cycloheteroalkyl, --.

At Column 35, Line 51, "$C_5$-$C_{16}$mheteroaralkyl," should be -- $C_5$-$C_{16}$heteroaralkyl, --.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*